United States Patent [19]

Dougherty et al.

[11] Patent Number: 5,027,824
[45] Date of Patent: Jul. 2, 1991

[54] METHOD AND APPARATUS FOR DETECTING, ANALYZING AND RECORDING CARDIAC RHYTHM DISTURBANCES

[76] Inventors: Edmond Dougherty, 523 W. Valley Rd., Strafford, Pa. 19087; George Simmons, 1821 Sycamore St., Haddon Hts., N.J. 08035

[21] Appl. No.: 444,644

[22] Filed: Dec. 1, 1989

[51] Int. Cl.⁵ .............................................. A61B 5/04
[52] U.S. Cl. .................................. 128/702; 128/696; 128/710
[58] Field of Search ...................... 128/696, 700–708, 128/710

[56] References Cited

U.S. PATENT DOCUMENTS

| | | | |
|---|---|---|---|
| 3,832,994 | 9/1974 | Bicher et al. | 128/702 |
| 4,622,979 | 11/1986 | Katchis et al. | 128/702 |
| 4,732,158 | 3/1988 | Sadeh | 128/702 |
| 4,742,831 | 5/1988 | Silvian | 128/696 |
| 4,896,677 | 1/1990 | Kaneko et al. | 128/696 |

*Primary Examiner*—Francis Jaworski
*Assistant Examiner*—George Manuel

[57] ABSTRACT

Apparatus for detecting, analyzing and recording cardiac events includes a patient-wearable monitor detecting cardiac events and cardiac rhythm and processing information indicative of those events and rhythm to detect presence of a disturbance in the monitored rhythm by recording selected data from the patient's electrocardiogram before, during and after a detectd cardiac rhythm disturbance.

19 Claims, 11 Drawing Sheets

METHOD AND APPARATUS FOR DETECTING, ANALYZING AND RECORDING CARDIAC RHYTHM DISTURBANCES

FIELD OF THE INVENTION

The principal focus of this invention is towards apparatus and methods for detecting, analyzing and recording cardiac rhythm patterns, particularly cardiac rhythm disturbances, for subsequent analysis, diagnosis and treatment of cardiac rhythm disturbances by physicians. In addition to detecting, analyzing and recording cardiac rhythm patterns, the invention has applicability to monitoring other physiological signals such as temperature, blood pressure, brain waves and the like.

LEXICOGRAPHY

Because this invention relates both to medicine, particularly cardiology, to electrical engineering and to software, the following glossary of terms is provided respecting the prior art and the invention disclosed herein:

ADM Technique—A method for digitizing an analog signal by comparing the analog signal to a signal derived from the analog signal and producing a digitized representation of the analog signal as a function of such comparison.

Algorithm—A sequence of instructions directing performance of a specific task, such as moving information or calculating values.

Arrhythmia—Irregularity of heartbeat.

Arrhythmic event—Cardiac behavior over a finite time period commencing with an arrhythmia.

Artifact—Undesirable, extraneous components appearing in an EKG as a result of muscle action and/or other external actions not related to cardiac function.

Asymptomatic—Lack of patient awareness that a particular condition exists within the patient.

Asystole—Absence of a heartbeat.

Bradycardia—Slow heart rate.

Complex—The portion of an EKG signal reflecting a single heartbeat.

EKG/ECG Electrocardiogram—An analog signal reflecting electrical activity of the heart.

Huffman Coding—A scheme for compressing digital data.

R-wave—A specific portion of the electrocardiogram reflecting cardiac behavior during a corresponding portion of a single heartbeat.

ST Segment Analysis—Study of a specific portion, different from the R-wave, of the electrocardiogram reflecting cardiac behavior during a selected portion of a single heartbeat.

Symptomatic—Patient awareness that a particular condition exists.

Tachycardia—Fast heart rate.

Ventricular—Having to do with the ventricular chamber of the heart.

VPC/PVC/Premature Ventricular Contraction—a single heartbeat occurring earlier than expected.

BACKGROUND OF THE INVENTION

Analysis of electrocardiogram data taken over extended periods provides clinically significant information which is important in the diagnosis and treatment of cardiac disease. Long-term recording of electrocardiographic data, commonly referred to as "Holter" monitoring, is a standard, accepted technique for electrocardiographic analysis. This amounts to recording electrocardiogram data over a period of time and subsequently analyzing that data for rhythmic and morphological changes.

Presently used monitoring devices for ambulatory patients are adequate for recording electrocardiogram data over twentyfour hour periods. However, presently used devices have limitations which come into play when longer term recording of electrocardiogram data is necessary.

Often it is desirable to monitor cardiac rhythm and disturbances in cardiac rhythm when the disturbances are highly variable in frequency or when the frequency of disturbances is very low. Current practice is to employ repetitive twenty-four hour cardiogram monitors. However, this is very expensive and results in significant discomfort to the patient due to the substantial size of the recording device required to record cardiac rhythm over twenty-four hour and longer periods.

For other patients, whose arrhythmia is symptomatic (meaning that the arrhythmia is related to a particular condition occurring in the patient's body which the patient can sense) a patient-activated cardiac event recorder is often used. These patient-activated cardiac event recorders are limited in the data they provide because the recorder must be activated by the patient. Obviously, if the arrhythmic event incapacitates the patient, the patient cannot activate the cardiac event recorder. Also, if the arrhythmic event is asymptomatic, a patientactivated cardiac event recorder cannot be used because the patient does not know when his or her arrhythmia is occurring.

Applicants are aware of printed prior art consisting of U.S. Pat. Nos. 4,123,785; 4,231,374; 4,333,475; 4,336,810 and 4,667,682.

The '785 patent discloses a cardiac event recorder for recording cardiac events over a defined twenty-four hour period. This device has the disadvantage associated with all patientactivated devices, namely if the arrhythmic event incapacitates the patient, the patient cannot activate the cardiac event recorder. Similarly, if the arrhythmic event is asymptomatic, a patient-activated device will never be turned on to record the arrhythmic event.

The '475 patent uses a microcomputer to continuously monitor analog electrocardiogram signals and execute algorithms to classify each heartbeat and tally abnormal events such as arrhythmia.

Similarly to '475, the 3 374 patent discloses a device and method for constantly monitoring heartbeat and activating circuitry upon occurrence of an abnormal heartbeat or other arrhythmic event to determine whether additional arrhythmic events occur during a selected subsequent monitoring period.

The '810 patent discloses method and apparatus for analyzing a Holter-type electrocardiogram utilizing a tape playback unit having an analog signal output representing electrocardiogram complexes.

The '682 patent discloses an ambulatory electrocardiogram recorder that senses tachycardia and bradycardia conditions and activates a tape recorder for a period of fifteen seconds after a traycardia or bradycardia event is detected.

SUMMARY OF THE INVENTION

In one of its aspects, this invention provides apparatus for detecting, analyzing and recording cardiac events, particularly cardiac rhythm disturbances. The apparatus aspect of the invention includes a patient-wearable means for monitoring cardiac events and cardiac rhythm and for processing signals indicative of cardiac events and particularly cardiac rhythm disturbances. The patient-wearable cardiac event monitoring and signal processing means preferably includes means for continuously monitoring cardiac rhythm and, optionally, other parameters indicative of cardiac status. Such monitoring is performed via electrocardiogram leads connected to a patient. The patient-wearable cardiac event monitoring means further includes means for detecting presence of a disturbance in the monitored cardiac rhythm. The patient-wearable monitoring means further includes means, operative responsively to the cardiac rhythm disturbance detecting means, for recording selected data from the patient's electrocardiogram before, during and after the detected cardiac rhythm disturbance. The means which is operative responsive to the cardiac rhythm disturbance detecting means preferably further includes means for periodically recording cardiac data, in addition to cardiac rhythm, which is indicative of cardiac function.

In the apparatus aspect, the invention may yet further include a base station for receiving the recorded and analyzed cardiac event and arrhythmia data, for further analyzing the data which are indicative of cardiac function, to provide information helpful to a cardiologist or other health professional.

Figure 1:
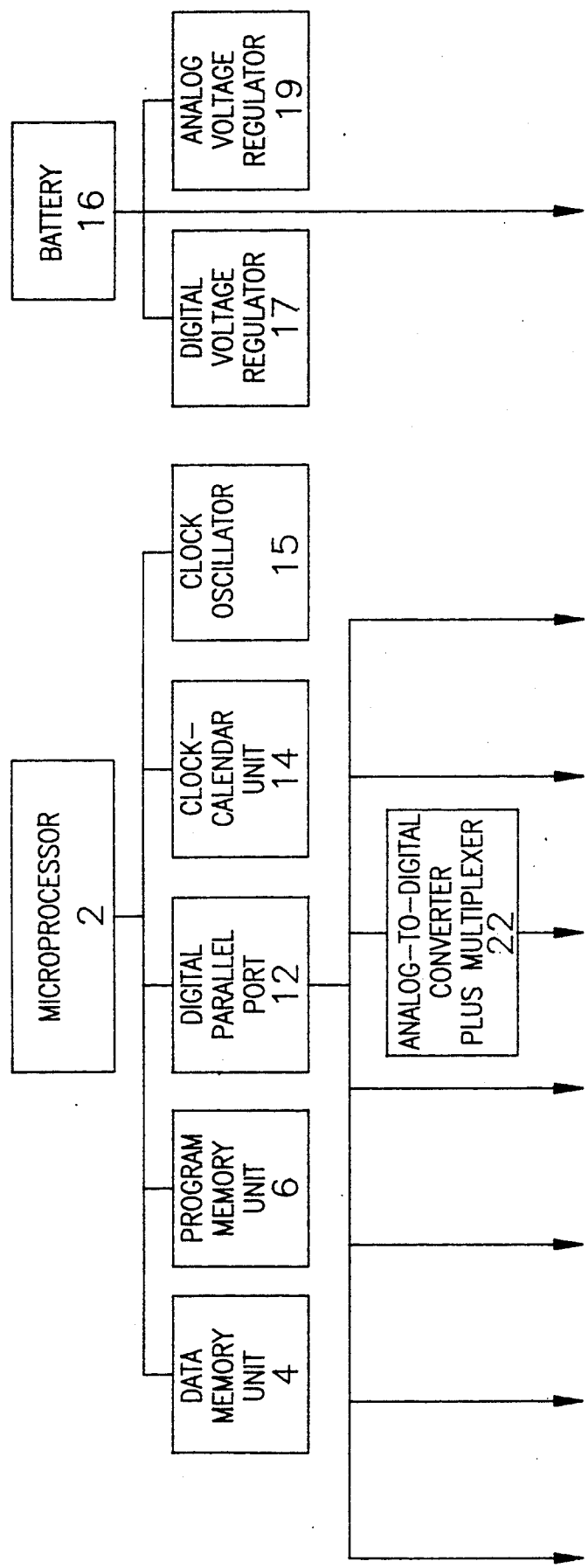
FIG. 1 is a block diagram schematically illustrating a portion of the patient-wearable cardiac event monitoring unit.

In the drawings, circuit elements which are substantially functional equivalents of one another in different embodiments of the invention are indicated using the same number. In some cases, prime notations associated with the number identifying a circuit element are used to indicate that such circuit element is a part of the preferred embodiment of the apparatus of the invention.

DESCRIPTION OF THE PREFERRED EMBODIMENTS AND BEST MODE KNOWN FOR PRACTICING THE INVENTION

Referring to FIG. 1, a microprocessor 2 has connected to it a data memory unit 4, a program memory unit 6, a digital parallel port 12, a clock-calendar unit 14 and a clock oscillator 15. Digital parallel port 12 connects an analog-to-digital converter 22, having a multiplexer as a part thereof, to microprocessor 2. The downwardly extending arrows in FIG. 1 denote plug connectable connections for connecting selected modules, each having components adapted to perform different monitoring functions, to microprocessor 2 and associated components illustrated in FIG. 1. The preferred selected module for connection to the microprocessor 2 and associated components illustrated in FIG. 1 is an arrhythmia analysis module, described below.

Figure 2:
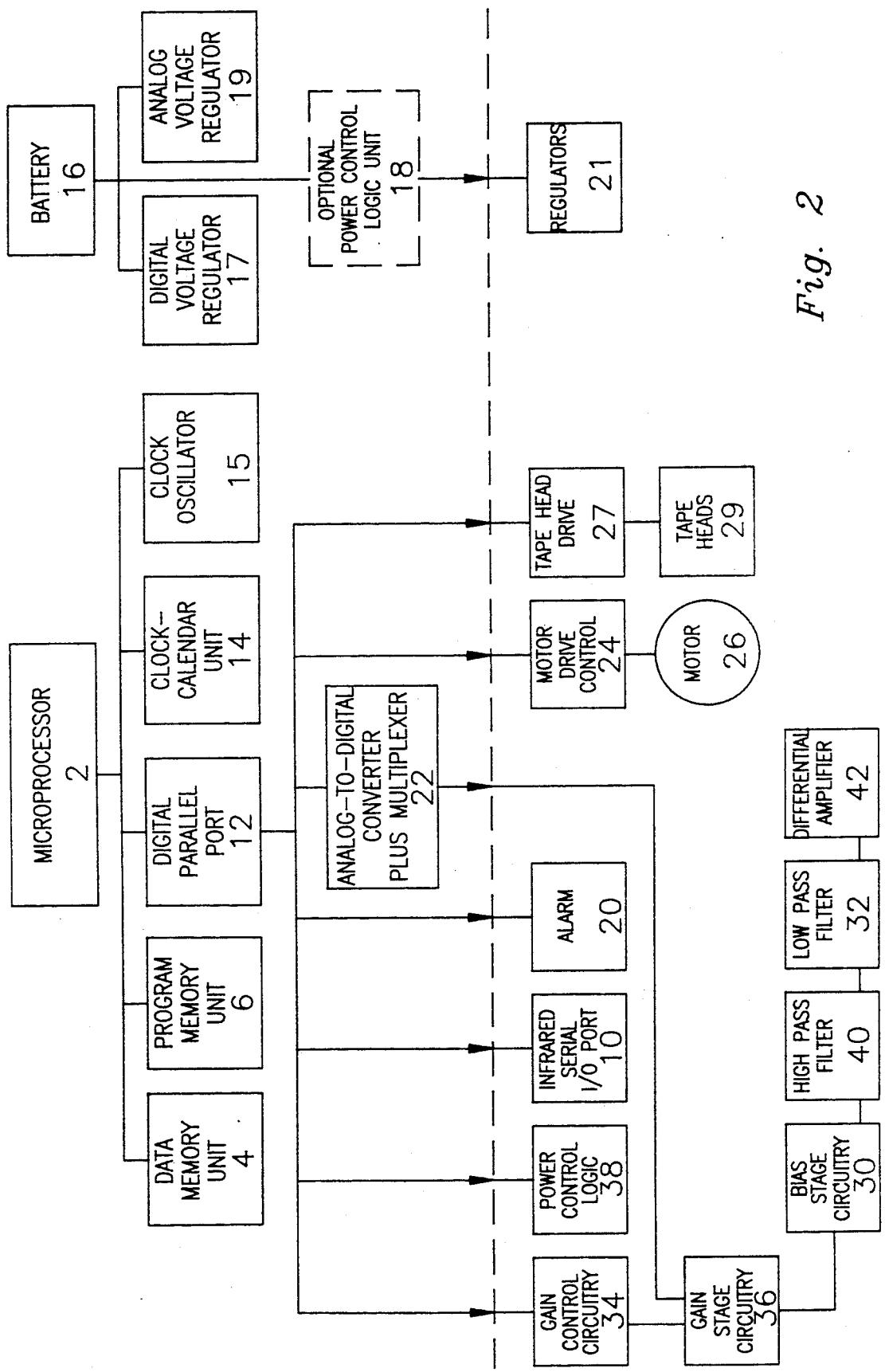
FIG. 2 is a block diagram similar to FIG. 1 showing in schematic form an arrhythmia analysis module connected to the cardiac event monitoring unit illustrated schematically in FIG. 1.

FIG. 2 schematically illustrates a particular module, specifically a preferred arrhythmia analysis module, plugconnected to the cardiac event monitoring unit illustrated schematically in FIG. 1. The broken line in FIG. 2 denotes the plug connection interface between the cardiac event monitoring unit and the arrhythmia analysis module.

The arrhythmia analysis module may or may not be fabricated on a printed circuit board separate from the circuitry of the cardiac event monitoring unit. Plug connection between the cardiac event monitoring unit and the arrhythmia analysis module is preferable and, accordingly, it is most desirable that the circuitry of the cardiac monitoring unit be on a printed circuit board separate from circuitry of the arrhythmia analysis module. Plug connection permits removal of the arrhythmia analysis module and substitution of another analysis module connected to the cardiac event monitoring unit so that other physiological phenomenon can be detected, analyzed and recorded, if desired.

In FIG. 2 the arrhythmia analysis module includes an infrared information sensing transistor and diode unit 10, an alarm 20, function specific arrhythmia module power control logic 38, gain control circuitry 34, gain stage circuitry 36, bias stage circuitry 30, high pass filter circuitry 40, low pass linear phase filter circuitry 32, instrumentation amplifier circuitry 42, motor drive control 24, a tape head drive 27, tape heads 29 and regulator(s) 21. As further evidenced from FIG. 2, gain stage circuitry 36 is connected to digital parallel port 12 leading to microprocessor 2 via gain control 34. Gain stage circuitry 36 is further connected to microprocessor 2 via digital parallel port 12 by means of analog-to-digital converter with multiplexer timer 22. Apparent from FIG. 2, the arrhythmia analysis module has multiple connections to digital parallel port 12 including gain control 34, powered down circuitry 38 which is sometimes referred to as function specific module power control logic circuitry, infrared serial input/output port 10, alarm 20, motor control circuitry 24 and tape head control circuitry 27. Input signals arrive at the first differential amplifier stage or circuitry 42 which connects in turn to low pass filter circuitry 32, high pass filter circuitry 40, offset adjustment circuitry 30 and adjustable gain stage circuitry 36. Adjustable gain stage circuitry 36 also connects to gain control circuitry 34 and to analog-to-digital converter/multiplexer 22.

As further apparent from FIG. 2, in the preferred embodiment gain stage circuitry 36 connects to bias stage circuitry 30. This bias stage circuitry 30 is in turn connected to high pass filter circuitry 40. This high pass filter circuitry 40 is in turn connected to low pass linear phase filter circuitry 32, which in turn is connected to instrumentation amplifier 42. In the preferred embodiment, input signals first arrive at differential amplifier stage 42 for processing thereby and by the elements schematically illustrated connected in series leading away from differential amplifier stage 42.

While motor 26 is shown schematically in FIG. 2, motor 26 does not form any portion of the arrhythmia analysis module; motor 26 is an integral part of the apparatus of the invention because motor 26 serves to drive the tape recorder portion of the apparatus of the invention.

The circuit elements in FIG. 1 are preferably static, complementary metal oxide silicon (CMOS) circuit elements. These CMOS elements provide low power consumption.

Figure 10:
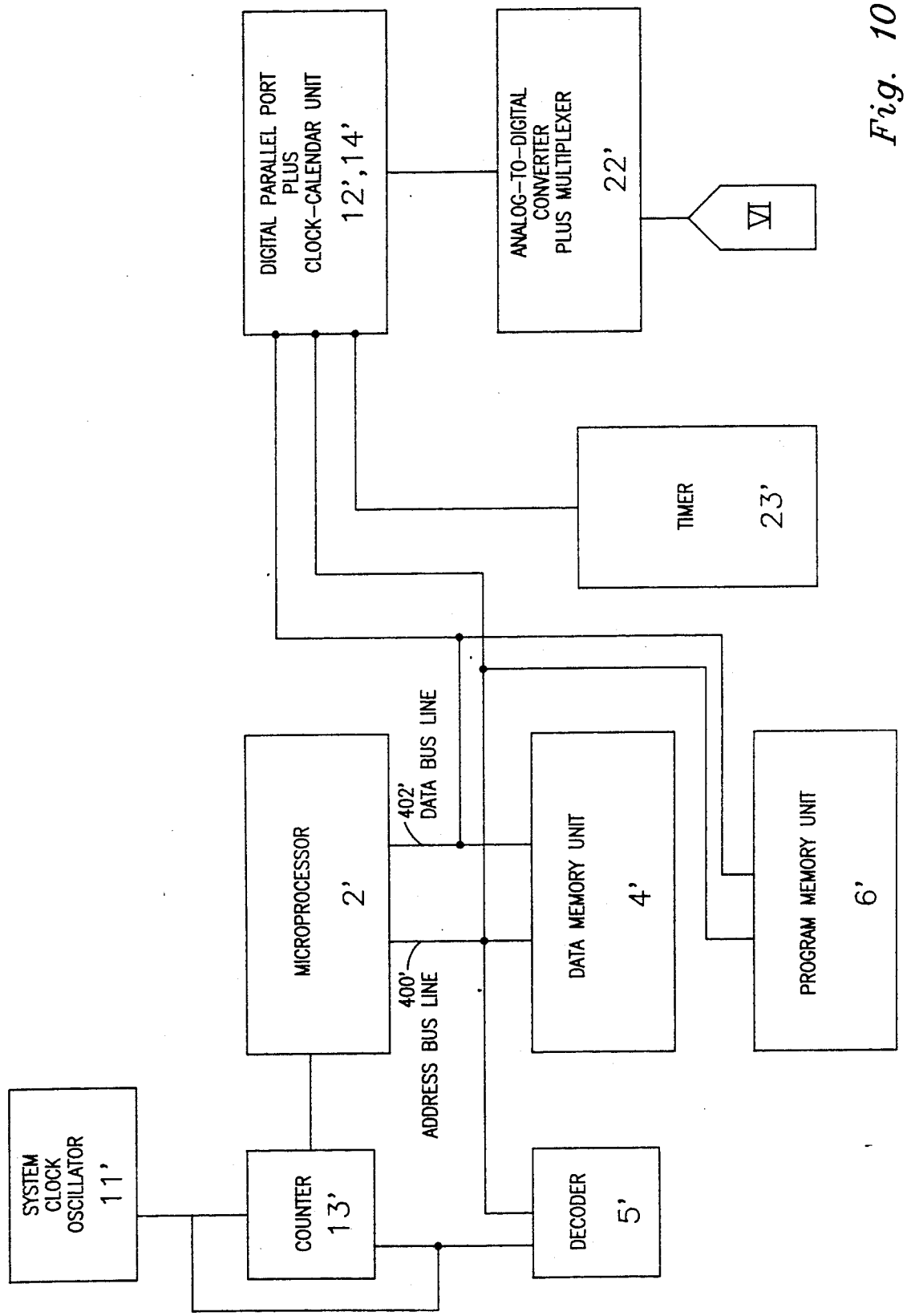
FIG. 10 is a schematic block diagram of the preferred embodiment of the digital circuitry used in the cardiac event monitoring unit/arrhythmia analysis module worn by the patient.

Further referring to FIG. 1, microprocessor 2 is preferably a member of the 6502 family. Specifically, microprocessor 2, shown with prime notation in FIG. 10, is preferably a Rockwell R65C02, package PLCC-44, part number R65C02J1, microprocessor of the 6502 family.

An optional power control logic unit 18, shown as a part of the arrhythmia analysis module in dotted lines in FIG. 2, may consist of a logic array and a number of low power analog switches. The optional power control logic unit 18 may be used to power down the unit, to a low power, quiescent operating state, during periods of inactivity.

The program memory 6 contains all of the fundamental subroutines required for operation of the cardiac monitor circuitry. These sub-routines include those performing analog-to-digital conversion, analog multiplexing, power control, tape control, tape recording, serial communications and data compression. Data memory 4 serves as the read-write random access memory for microprocessor 2. Program variables and stacks are stored in the random access memory portion of data memory 4. Preferably infrared serial input/output unit 10 may be provided to communicate with the base station portion of the apparatus of the invention. The base station is preferably a personal computer. Preferably infrared serial input/output unit 10 communicates with the base station via an infrared sensing transistor and diode unit, which eliminates the need for a cable connector between the base station computer and the cardiac event monitor.

Digital parallel port 12 includes general purpose digital input/output lines. In the preferred embodiment of the invention, certain of these digital input/output lines are dedicated to control the analog-to-digital converter multiplexer 22. Preferably, the remaining lines are reserved for a particular application module such as the arrhythmia analysis module.

Analog-to-digital converter with multiplexer 22 serves to digitize analog signals for analysis by microprocessor 2 or for storage in the random access memory portion of data memory unit 4 or for recording on magnetic tape by tape heads 29. A single analog-to-digital converter can digitize several sources of analog signals; hence, an analog multiplexer is included as a portion of unit 22. The analog multiplexer allows microprocessor 2 to select one of several analog signals to pass through to the analog-to-digital converter for digitization. When the cardiac event monitor is working with the arrhythmia analysis module, preferably one analog channel is used. The channel carries the electrocardiogram signal, conditioned to comply with AAMI standards for diagnostic electrocardiographic devices. Optionally, a second channel may also be used, carrying the same electrocardiogram signal, but being much more heavily filtered and conditioned. Microprocessor 2 may use either the optional heavily filtered and conditioned signal or the signal as conditioned only to the extent to comply with AAMI Standards to determine whether a cardiac event has occurred. Whether or not the heavily filtered signal is used, the lightly filtered electrocardiogram signal is stored in the random access memory portion of data memory unit 2 and, if it is determined after analysis that a cardiac event has occurred, is also stored by recording on the magnetic tape of the tape recorder. In the preferred practice of the invention, only a single channel is used. Microprocessor 2 uses the electrocardiogram signal in an only lightly conditioned form, preferably conditioned only to the extent to comply with all AAMI standards, to determine whether a cardiac event has occurred.

If desired, the software in microprocessor 2 can be programmed so that alarm 20 signals the patient as to occurrence of a given, predetermined state. Depending on the option selected during programming, alarm 20 may sound upon detection of a hardware problem such as a low battery, low tape remaining or the like. Alternatively, the alarm may sound because the cardiac monitor has recognized a cardiac event. The user has the option to have alarm 20 sound in the event of only certain types of arrhythmias, or upon occurrence of any arrhythmias, according to programming of the system.

Clock/calendar unit 14 maintains the date and time. Clock/calendar unit 14 preferably is contained within digital parallel port 12.

When a cardiac event has occurred and the random access memory of data memory unit 4 is full, the cardiac event data is recorded on magnetic tape by a tape recorder driven by motor 26. Microprocessor 2 instructs digital parallel port 12 to generate a motor control signal as input to motor drive control 24, which turns motor 26 on and off based on control commands received from microprocessor 2. The design goal has been to achieve time response of microprocessor 2 and motor drive control 24 such that the motor is up to proper speed in approximately eight one-thousandths (0.008) seconds and stops in the same time or even less.

Drive motor 26 may be a pulse/continuous motor having a time constant of approximately seven milliseconds. In one - practice of the invention, motor 26 has been driven by a regulated voltage of nominally 2.2 volts. Drive motor 26 should stop almost instantly upon a short circuit of its input. Since drive motor 26 has a design goal of reaching running speed at about five times its time constant or in about 35 milliseconds and since creating a true short circuit at the input for drive motor 26 is not straightforward, the start and stop times of the motor may be controlled using specially shaped motor pulses produced by motor drive control circuitry 24. This approach reduces wasted tape space, particularly in applications where only small quantities of data are recorded, either periodically or aperiodically.

In one practice of the invention, a Radio Shack micro-26 cassette recorder has provided the basis for the tape recorder in the cardiac monitor unit.

Battery module 16 preferably houses two Electrochem 3B793-TC lithium batteries. While lithium batteries are currently preferred, zinc-air, aluminum-air or alkaline batteries may also possibly be used with the invention. Having these two on-board batteries is one approach permitting use of voltages below an arbitrary local ground level. With this approach, stop time of motor 26 may be virtually equivalent to that which would be experienced if the input to motor 26 was short-circuited. Motor 26 start time may be reduced as a result of improved acceleration at motor turn-on provided by appropriately shaping the run-pulse onset voltage versus time curve.

One design goal is to have the capstan of motor drive 26 operate at about 7,500 revolutions per minute, to drive a 181:1 reduction gear train. One design goal for motor output shaft rotation is about 0.6906 revolutions per second. The design goal for motor torque is about 0.052 inch-ounces with the gear train output torque being about 9.412 inch-ounces, which is far above that required by the tape recorder for tape movement.

Another design goal is to have the drive motor capstan with a diameter of about 0.1248 inches, to result in a circumference of about 0.3921 inches. When the motor capstan is driven at the design goal of about 0.6906 revolutions per second, the magnetic tape should move at a rate of about 0.2708 inches/second. Assuming a conservative pulse-packing factor of 4,500 bits/inch/track, this means that it should be possible to write on the tape every $222 \times 10^{-6}$ inches at a data-writing rate of 1,220 nibbles/second, assuming a four-track tape.

Lithium thionyl chloride batteries may be used in place of the preferred Electrochem lithium batteries noted above. Such lithium thionyl chloride batteries have extremely stable voltage levels, very high energy capacity per unit volume and extremely low density. If 95% of the capacity of the batteries is used, such a battery pair should easily accommodate between six and twelve patients each using the cardiac monitor apparatus of the invention for seventeen days or less.

One of the advantages of the invention is that the cardiac monitor unit may be programmed, using suitable algorithms, to automatically calculate its own battery usage and to report such battery usage information to the base station computer via the infrared coupling provided by infrared sensing transistor and diode unit 10. Accordingly, the base station computer may inform the medical technician or physician of battery status and may specify when batteries in a cardiac monitor unit according to the invention must be changed. A safety factor may be built-in to insure that the batteries in the cardiac monitor unit do not run out while the unit is being worn by a patient. The batteries should be designed so that short-circuiting produces no serious or dangerous consequence to the patient; appropriately applied diodes throughout most of the cardiac monitor unit and arrhythmia analysis module protect the circuitry against adverse consequences in the event the batteries short-circuit.

Referring to FIG. 2, instrumentation amplifier 42, sometimes descriptively referred to as differential amplifier 42, preferably utilizes three quarters of two Precision Monolithics, Inc. Quad Precision operational amplifiers, package SOL-16, part number OP490GS, to obtain a quality single lead of electrocardiogram signal, as shown in greater detail in FIGS. 4 and 5. The instrumentation amplifier circuitry designated generally 42 in FIG. 2 and in FIG. 4 and 42' in FIG. 5 has a differential input with high impedance and high common mode rejection. Signals from the two electrodes of an electrocardiogram measuring device, designated 44, 46, are the plus and minus inputs to instrumentation amplifier 42 or 42'. A third electrode 48 from the electrocardiogram acts as a reference and is connected to the negative ground for the analog circuitry portion of the invention, as indicated by the inverted triangle with the subscript A in FIG. 5. (The analog circuitry portion of the invention, as disclosed in two embodiments, is generally shown in FIGS. 4 through 9 of the drawings. The inverted triangle with the subscript A is used throughout the drawing figures to denote ground reference for the analog portion of the circuitry of the invention. For the digital portion of the circuitry of the invention, a ground reference is indicated in the drawings by the conventional ground symbol, consisting of four parallel horizontal lines of decreasing length, disposed in a generally triangular shape. This symbol is used extensively in FIG. 3.)

Figure 4:
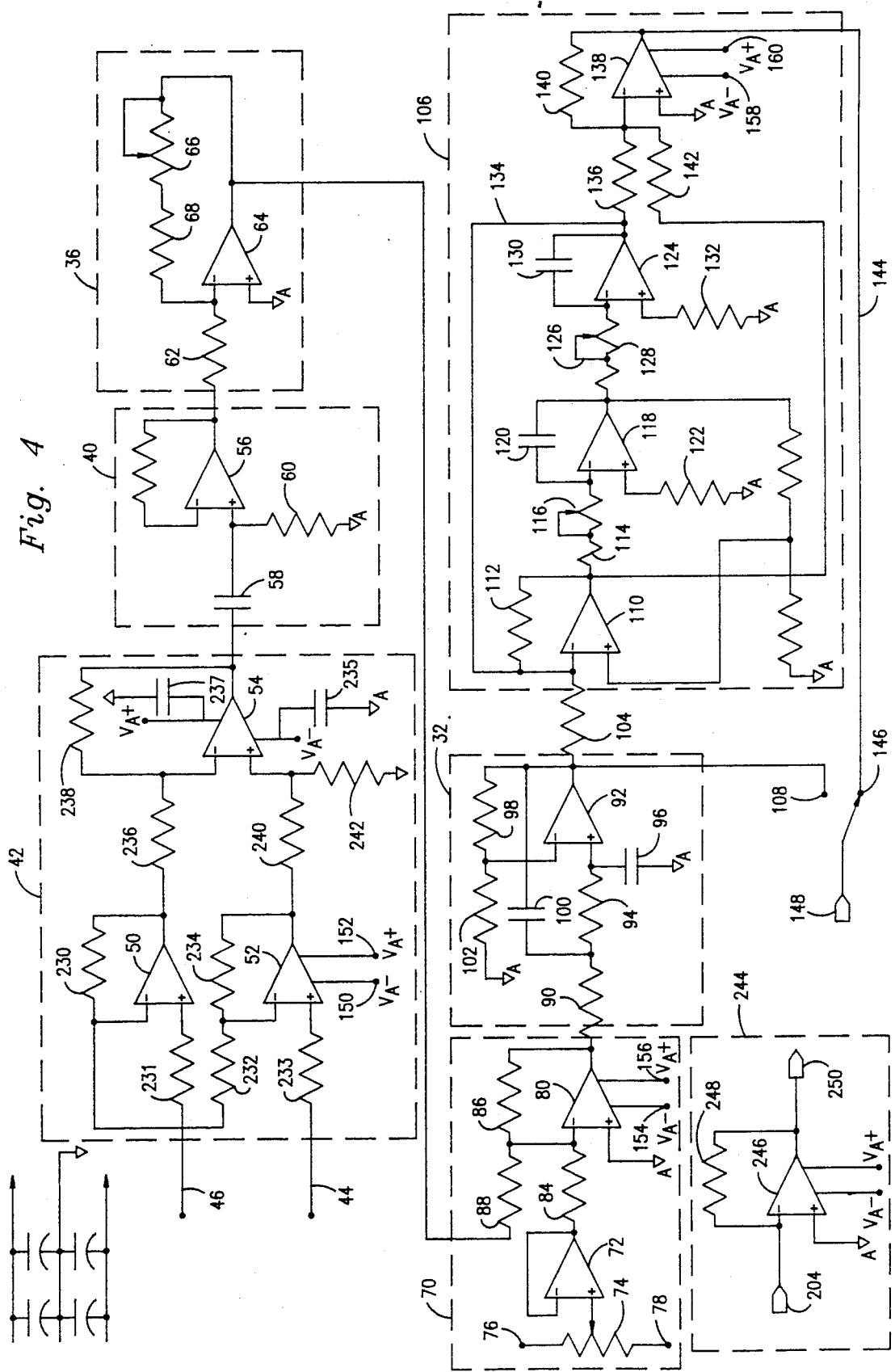
FIG. 4 is a schematic diagram of one embodiment of analog circuitry which may be used in the cardiac event monitoring unit and arrhythmia analysis module.
Figure 5:
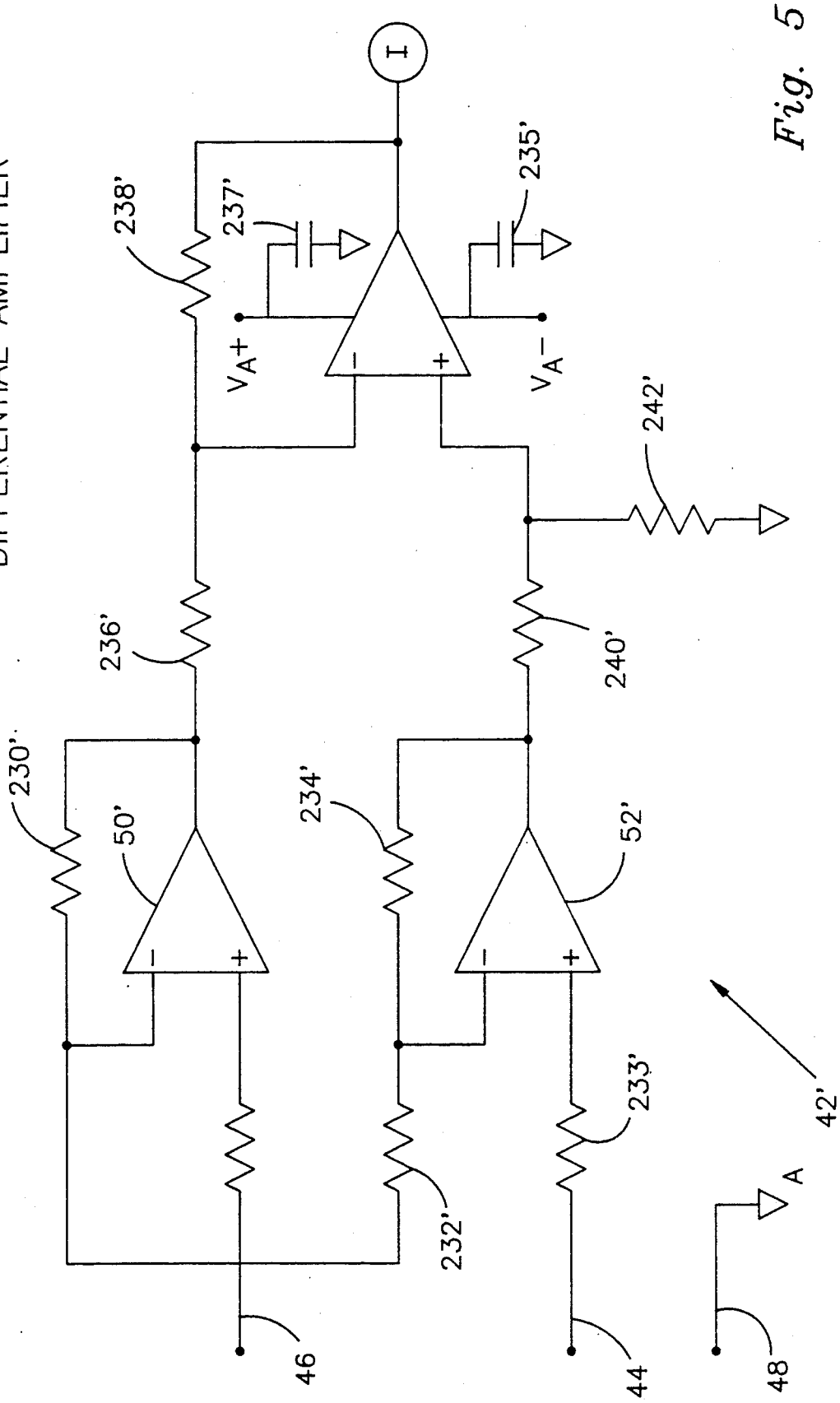
FIG. 5 is a schematic diagram of a preferred embodiment of differential amplifier circuitry used as a portion of the analog circuitry in a preferred embodiment of the cardiac event monitoring unit/arrhythmia analysis module worn by the patient.

In FIGS. 4 and 5, where circuitry of instrumentation amplifier 42 or 42' is shown in greater detail, three sections of the OP490 operational amplifier identified herein as differential amplifier 42 are designed 50, 52 and 54. Further respecting instrumentation amplifier 42, output of operational amplifier 50 is provided as feedback to the negative input terminal thereof via resistor 230. This signal is also provided, through resistor 232 to combine with output signal from operational amplifier 52 as provided through resistor 234 as feedback input to the negative input terminal of operational amplifier 52. Output of operational amplifier 50 is also provided via resistor 236 for combination with output from operational amplifier 54 provided through resistor 238 for input to the negative input terminal of operational amplifier 54. Output of operational amplifier 52 is provided through resistor 240 as input to the positive input terminal of operational amplifier 54. Resistor 242 connects the positive input terminal of operational amplifier 54 to a voltage source.

Referring again to FIG. 2, high pass filter circuitry 40 removes the DC component from the electrocardiogram signal after processing by instrumentation amplifier 42. High pass filter circuitry 40 is preferably a single pole passive circuit which passes frequencies of 0.1 Hertz and higher. One embodiment of high pass filter circuitry 40 is shown in greater detail in FIG. 4. High pass filter circuitry 40, capacitor 58 and resistor 60 provide filtered input to operational amplifier 56 for processing to produce an output signal from high pass filter circuitry 40.

Figure 7:
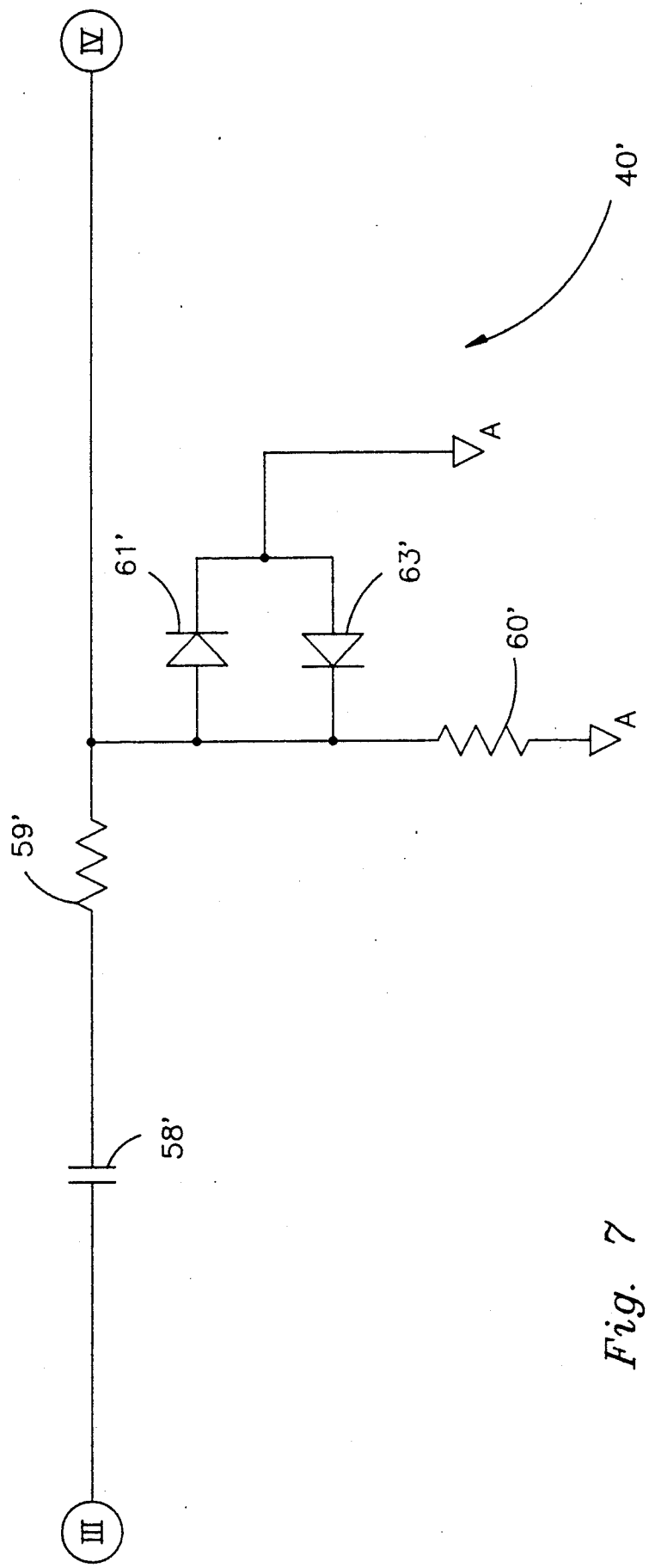
FIG. 7 is a schematic diagram of a preferred embodiment of high pass filter circuitry used as a portion of the analog circuitry in a preferred embodiment of the cardiac event monitoring unit/arrhythmia analysis module worn by the patient.

The preferred embodiment of high pass filter circuitry is illustrated in FIG. 7 where the filter circuitry receives input signal as indicated by III and includes a capacitor 58', a resistor 59', a resistor 60' and diodes 61' and 63' connected in the manner illustrated between the main signal line and analog ground. Capacitor 58' is preferably a 2.2 microfarrad Illinois capacitor part number 225BPR050MXXAF. Resistor 59' is preferably a 1 K ohm carbon film resistor. Resistor 60' is preferably a 1 M ohm carbon film resistor. Diodes 61, and 63, are preferably Motorola MMBD914 diodes. Output of high pass filter circuitry 40' is provided as indicated at IV in FIG. 7.

Details of the circuitry of one embodiment of gain stage 36 are illustrated in FIG. 4. Gain stage 36 includes an input resistor 62, an operational amplifier 64, variable potentiometer 66 and feedback resistor 68. Input to gain stage 36 is provided via bias resistor 62 to the negative input terminal of operational input amplifier 64. The positive input terminal of operational amplifier 64 is connected to ground. The portion of the output of operational amplifier 64 is provided as feedback to the negative input terminal of operational amplifier 64 via variable potentiometer 66 and resistor 68. Gain stage 36 amplifies the signal input thereto so that it is in the range of from 10 to 40, providing an overall gain of from 250 to 1,000.

Figure 9:
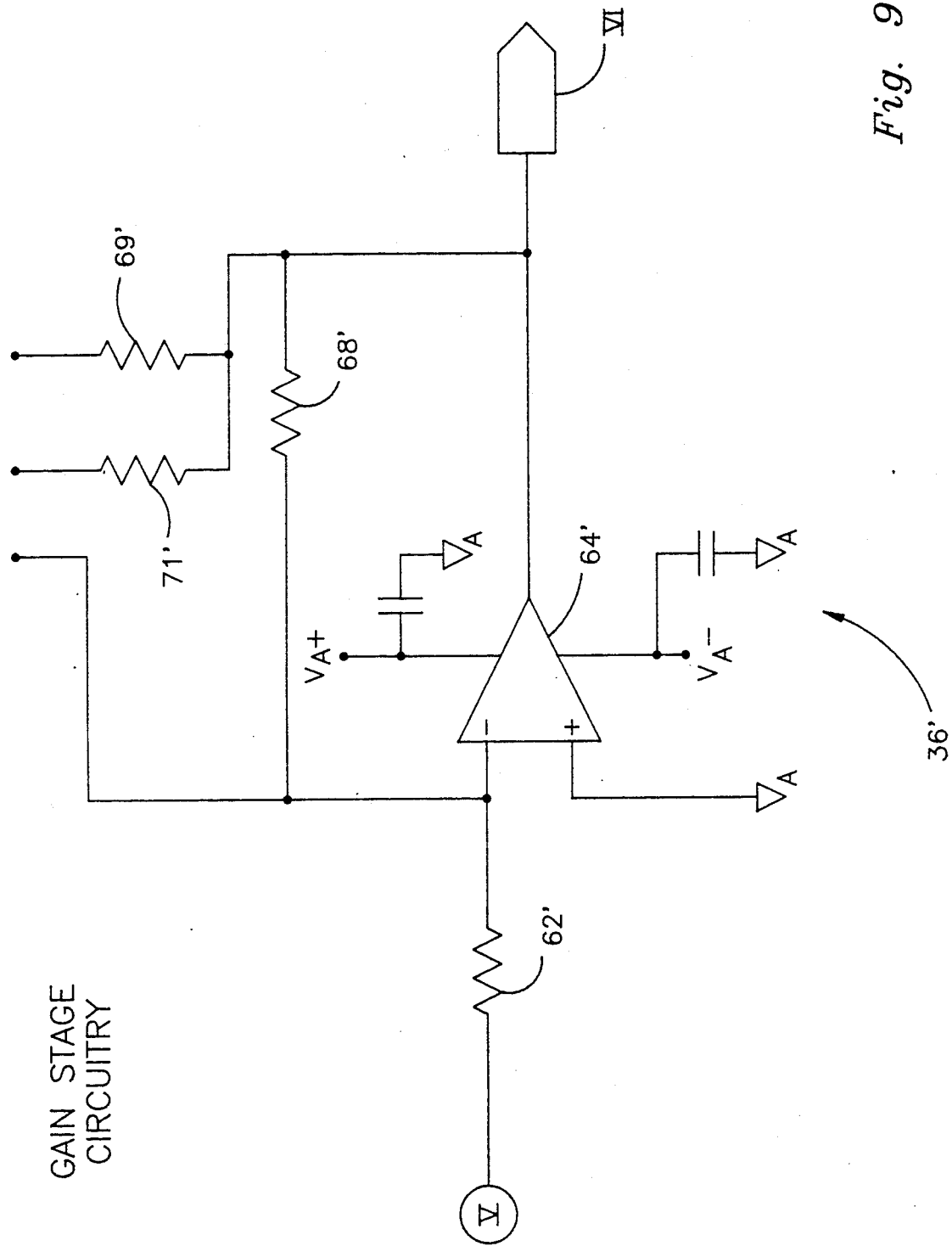
FIG. 9 is a schematic diagram of a preferred embodiment of adjustable gain stage circuitry used as a portion of the analog circuitry in a preferred embodiment of the cardiac event monitoring unit/arrhythmia analysis module worn by the patient.

A preferred embodiment of gain stage 36' is illustrated in FIG. 9 and receives its input signal as indicated by V. Input signal is processed through resistor 62', which is preferably a 56 K ohm carbon film resistor and received by quad operational amplifier 64', preferably a PMI quad operational amplifier, package SOL-16, part number OP490GS. Power is input to operational amplifier 64' via a line indicated as being connected to voltages $V_A+$ and $V_A-$. Quad operational amplifier 64' is preferably protected from surges and spikes by appropriate protection capacitors, unnumbered in FIG. 9, which connect the input power voltage lines to analog ground as illustrated in FIG. 9. (The same protection scheme is used many places throughout the preferred analog circuitry of the invention.) Further illustrated in FIG. 9, three terminals, unnumbered, appearing at the uppermost portion of the drawing, indicate a switch selectable among three settings to switch feedback resistors 68', 69' and 71' into and out of the feedback loop for amplifier 64'. Feedback resistor 68 is preferably a 1 M ohm carbon film resistor. Feedback resistor 69 is preferably also a 1 M ohm carbon film resistor while feedback resistor 71' is preferably a 470 K ohm carbon film resistor.

In one embodiment of the analog circuitry portion of the invention as illustrated in FIG. 4, output from gain stage 36 is provided to offset adjustment circuitry designated 70 and indicated generally by the so-numbered dashed line box in FIG. 4. This embodiment of the offset adjustment circuitry 70 includes operational amplifier 72, having its positive input terminal connected to a variable potentiometer 74 which in turn is connected between a source of positive and negative voltage, preferably plus and minus five volts at terminals 76, 78 as illustrated in FIG. 4. The source of positive and negative voltage is the same source of power voltage for the analog circuitry portion of the invention as discussed above respecting amplifier 64' shown in FIG. 9. This embodiment of the offset adjust circuitry illustrated in FIG. 4 further includes a second operational amplifier 80 receiving output of operational amplifier 72 via resistor 84, with operational amplifier 80 receiving such output as input at its negative terminal. Operational amplifier 80 further receives a portion of its output as input at its negative input terminal through a bias resistor 86 and yet additionally receives output of gain stage 36 through resistor 88 with both the output of gain stage 36 and the feedback of operational amplifier 80 being joined prior to application to the negative input terminal, operational amplifier 80. The positive input terminal operational amplifier 80 is connected to ground, as shown.

Figure 8:
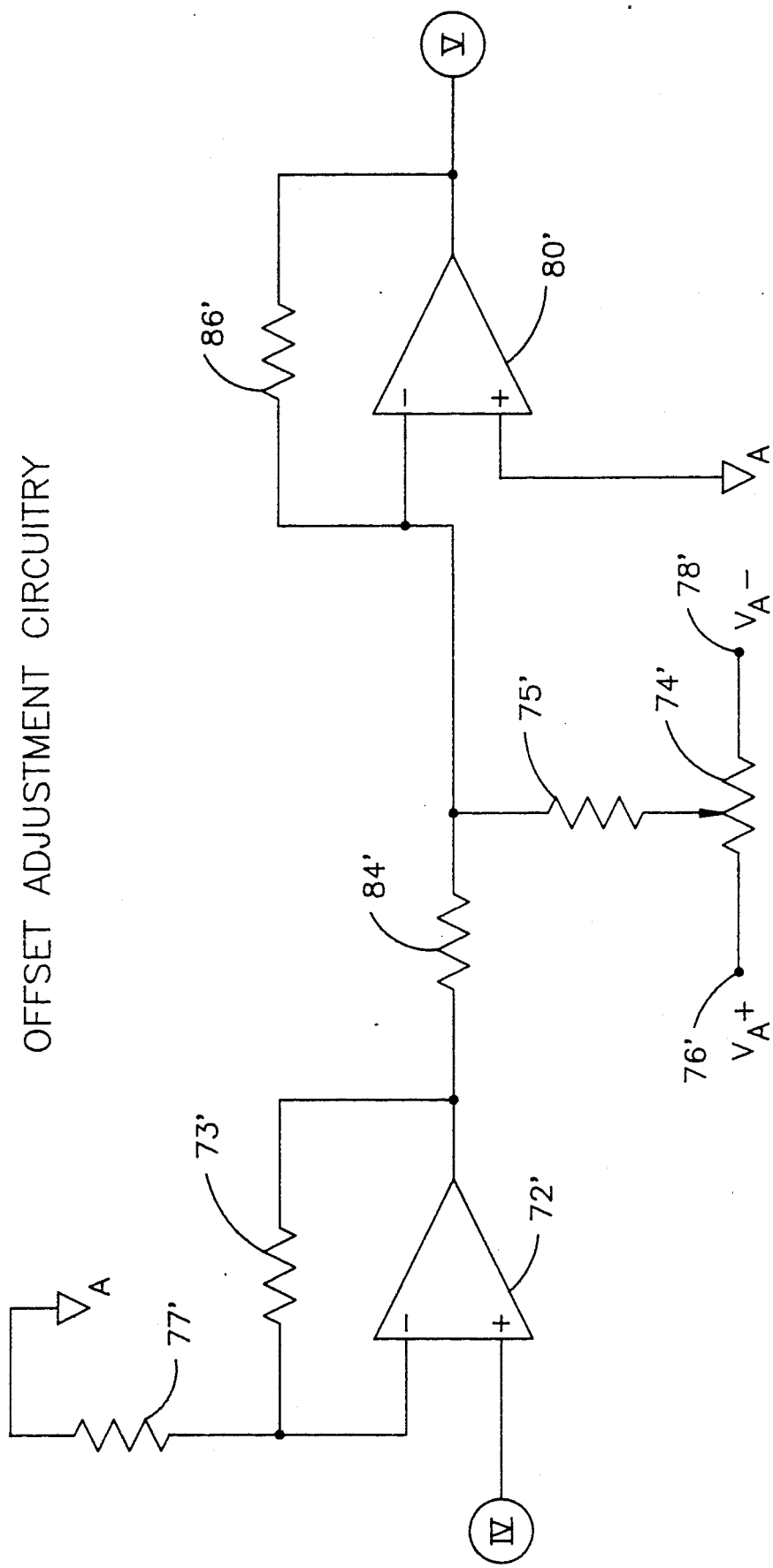
FIG. 8 is a schematic diagram of a preferred embodiment of offset adjust circuitry used as a portion of the analog circuitry in a preferred embodiment of the cardiac event monitoring unit/arrhythmia analysis module worn by the patient.

The preferred embodiment of the offset adjust circuitry is designated generally 70' in FIG. 8 and receives as its input, as illustrated by IV, the output of high pass filter 40'. This input signal is received at the positive terminal of an amplifier 72' which is also preferably a PMI quad operational amplifier, package SOL-16, part number OP490GS. Input of amplifier 72' is provided via feedback resistor 73'; resistor 73' is preferably a 1 M ohm carbon film resistor. Additionally, the negative input terminal of amplifier 72' is connected to analog ground, as illustrated, via resistor 77' which is also preferably a 1 M ohm carbon film resistor. Output of amplifier 72' is provided via resistor 84' as input, subject to appropriate biasing by signal received through resistor 75', to the negative input terminal of amplifier 80'. Resistor 84' is preferably a 56 K ohm carbon film resistor.

Amplifier 80' is preferably of the same type and manufacture as amplifier 72'. Bias resistor 75' is preferably a 1 M ohm carbon film resistor which in turn is connected to a variable potentiometer or variable resistor 74'. The preferred variable potentiometer 74' is preferably an ST-5W-100 K multiturn potentiometer made by Mepcopal. Input terminals to the variable potentiometer, designated 76', 78' in FIG. 8, are preferably connected to the source of input power voltage for the analog portion of the circuitry of the invention, as indicated by $V_A+$ and $V_A-$ at terminals 76', 78' respectively in FIG. 8. Output of amplifier 80' is fed back to the negative input terminal thereof via feedback resistor 86' which is preferably a 1 M ohm carbon film resistor. The positive input terminal of amplifier 80' is connected to analog ground as shown in FIG. 8. Output of the preferred embodiment of the offset adjustment circuitry is provided at V as shown in FIG. 8.

In the embodiment of the analog circuitry of the invention illustrated in FIG. 4, low pass linear phase filter circuitry denoted generally 32 in FIG. 4 receives as its input the output from offset adjustment circuitry 70 via resistor 90. Low pass filter circuitry 32 further includes an operational amplifier 92, a filter defined by resistor 94 and capacitor 96 providing filtered input to the positive input terminal of operational amplifier 92, a feedback resistor 98, a capacitor 100 and a resistor 102 connected to analog ground. Capacitor 100 provides a clipped portion of the output of operational amplifier 92 as feedback to the positive input terminal of operational amplifier 92 through the filter defined by resistor 94 and capacitor 96. A further portion of the output of the operational amplifier 92 is provided as feedback to the negative input terminal thereof via resistor 98.

In the embodiment of the analog circuitry of the invention illustrated in FIG. 4, low pass filter circuitry 32 filters the amplified electrocardiogram signal with a cut-off frequency of 100 Hertz in accordance with the AAMI standard for diagnostic electrocardiographic devices. Low pass filter circuitry 32 cuts off many high frequency artifacts. Output from low pass filter circuitry 32 is provided to the analog multiplexer via terminal 108 for digitization by the analog-to-digital converter and storage in random access memory portion of data memory 4 illustrated in FIGS. 1 and 2. The signal also enters the notch filter, for further processing, whereupon the processed signal may be used by microprocessor 2 for decision making.

Figure 6:
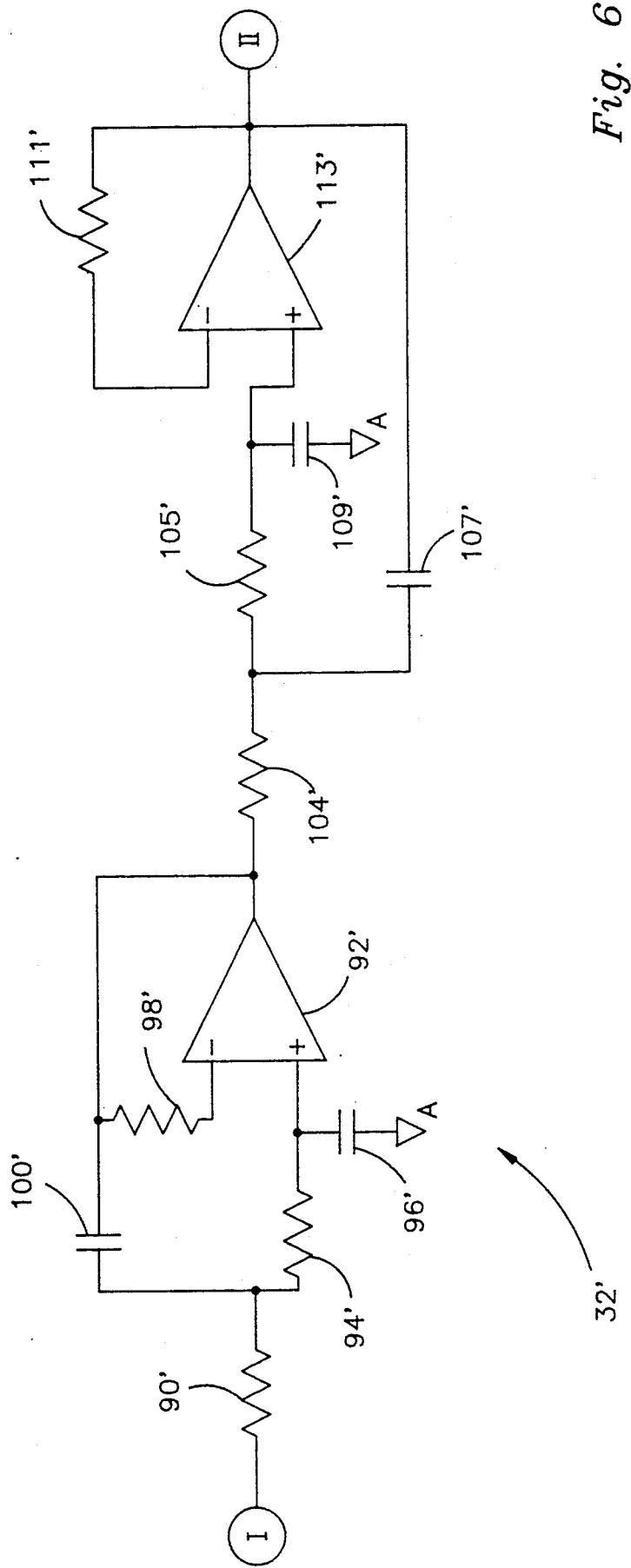
FIG. 6 is a schematic diagram of a preferred embodiment of low pass filter circuitry used as a portion of the analog circuitry in a preferred embodiment of the cardiac event monitoring unit/arrhythmia analysis module worn by the patient.

The preferred embodiment of the low pass filter circuitry of the analog portion of the circuitry of the invention is illustrated in FIG. 6 and designated generally 32'. In the preferred embodiment of the invention, low pass filter circuitry 32' receives as input the output of differential amplifier circuitry illustrated in FIG. 5 as indicated by I in FIG. 6. Loss pass filter circuitry includes resistor 90' which is preferably a 75 K ohm carbon film resistor. Loss pass filter circuitry 32' further includes resistor 94' and capacitor 96' serving as a filter for the input provided to positive input terminal of amplifier 92'. Resistor 94' is preferably a 75 K ohm carbon film resistor while capacitor 96' is preferably a 0.022 microfarrad capacitor manufactured by Mepco, part number C223K1206XFLB. Capacitor 96' connects to analog ground as shown.

Amplifier 92' is preferably a quad operational amplifier manufactured by PMI, package SOL-16, part number OP490GS, of the same type as generally described above. Low pass filter circuitry further includes a capacitor 100' via which output of amplifier 92' is provided as feedback to the positive input terminal thereof; capacitor 100' is preferably a 0.047 microfarrad capacitor available from Mepco, part number C473K1206XFLB. A portion of the output of amplifier 92' is provided as feedback to the negative input terminal thereof via resistor 98' which is preferably a 150 K ohm carbon film resistor.

Output from amplifier 92' passes through resistor 104', which is preferably a 75 K ohm carbon film resistor and through resistor 105', which is also preferably a 75 K ohm carbon film resistor to the positive input terminal of amplifier 113'. Amplifier 113' which is also preferably a PMI quad operational amplifier, package SOL-16, part number OP490GS, as generally described above. Resistor 105' in combination with capacitor 109' provides a filter for the signal input to the positive input terminal of amplifier 113'. Capacitor 109', which is connected to analog ground as shown, is preferably a 0.022 microfarrad capacitor available from Mepco, part number C223K1206XFLB. Output of amplifier 113' is fed back, to be provided as a portion of the input to the positive input terminal thereof through capacitor 107' which is also preferably a 0.047 microfarrad capacitor available from Mepco, part number C473K1206XFLB. Output of amplifier 113' is further provided as feedback input to the negative input terminal thereof via resistor 111' which is preferably a 150 K ohm carbon film resistor. Output of the preferred embodiment of the low pass filter circuitry portion of the analog circuitry of the invention is provided at II as indicated in FIG. 6.

In the embodiment of the analog portion of the circuitry of the invention illustrated in FIG. 4, output of low pass filter circuitry 32 is provided via resistor 104 as input to a 60 Hertz notch filter designated generally 106 in FIG. 4. Notch filter circuitry 106 may be provided to eliminate 60 Hz interference in the arrhythmia analysis module and includes operational amplifier 110 receiving input to the notch filter circuitry at its negative input terminal and a feedback resistor 112 providing a portion of the output of operational amplifier 110 as feedback to the negative input terminal thereof. This optional notch filter further includes resistor 114 and variable resistor 116 providing output of operational amplifier 110 as input to the negative terminal of operational amplifier 118. Output of operational amplifier 118 is cut-off for feedback to the negative input terminal thereof by capacitor 120. The positive input terminal of operational amplifier 118 is connected to ground via bias resistor 122. Output of operational amplifier 118 may be further provided to operational amplifier 124 via resistor 126 and variable resistor 128. Output of operational amplifier 124 is further provided as feedback input thereto, to the negative input terminal of operational amplifier 124, via a capacitor 130 which cuts off frequencies below a selected value. The positive input terminal of operational amplifier 124 is connected to ground via bias resistor 132.

In the embodiment of the analog circuitry of the invention shown in FIG. 4, output of operational amplifier 124 is further provided as feedback input to the negative terminal of operational amplifier 110 via feedback line 134. Output of operational amplifier 124 is further provided via resistor 136 as input to the negative terminal of operational amplifier 138. Output of operational amplifier 138 is also provided as feedback to the negative input terminal thereof via resistor 140. Further provided as input to the negative terminal of operational amplifier 138 is the output of operational amplifier 110 via resistor 142. The positive input terminal of operational amplifier 138 is connected to ground. The output of operational amplifier 138 is further provided via line 144 input to the digital section at terminal 146, by optional selection between the conditioned electrocardiogram signal provided at terminal 108 and the conditioned electrocardiogram signal having been subjected to the 60 Hertz notch filter provided at terminal 146. This selection is controlled using switch 148.

In the preferred embodiment of the analog circuitry of the invention, illustrated in FIGS. 5 through 9, no notch filter is used. This is because the upper cut-off frequency using this embodiment of this invention is 50 Hz and, accordingly, a 60 Hz notch filter would be redundant.

In the embodiment of the analog circuitry of the invention illustrated in FIG. 4, gain of operational amplifiers 52, 80 and 138 is controlled by variable input provided via pair of terminals 150, 152 for operational amplifier 52; pair of terminals 154, 156 for operational amplifier 80 and pair of terminals 158, 160 for operational amplifier 138. Terminals 152, 156 and 158 are preferably connected to a positive five volt source, namely the source of power voltage for the analog circuitry of the invention, designated $V_A+$, while terminals 152, 156, 160 are preferably connected to a negative five volt source, also namely the source of power for the analog circuitry of the invention, designated $V_A-$. Gain of these operational amplifiers is controlled by variable potentiometers connected to these preferably plus and minus five volt sources of power for the analog circuitry portion of the invention as designated by $V_A+$ and $V_A-$; these variable potentiometers are not illustrated.

Figure 3:
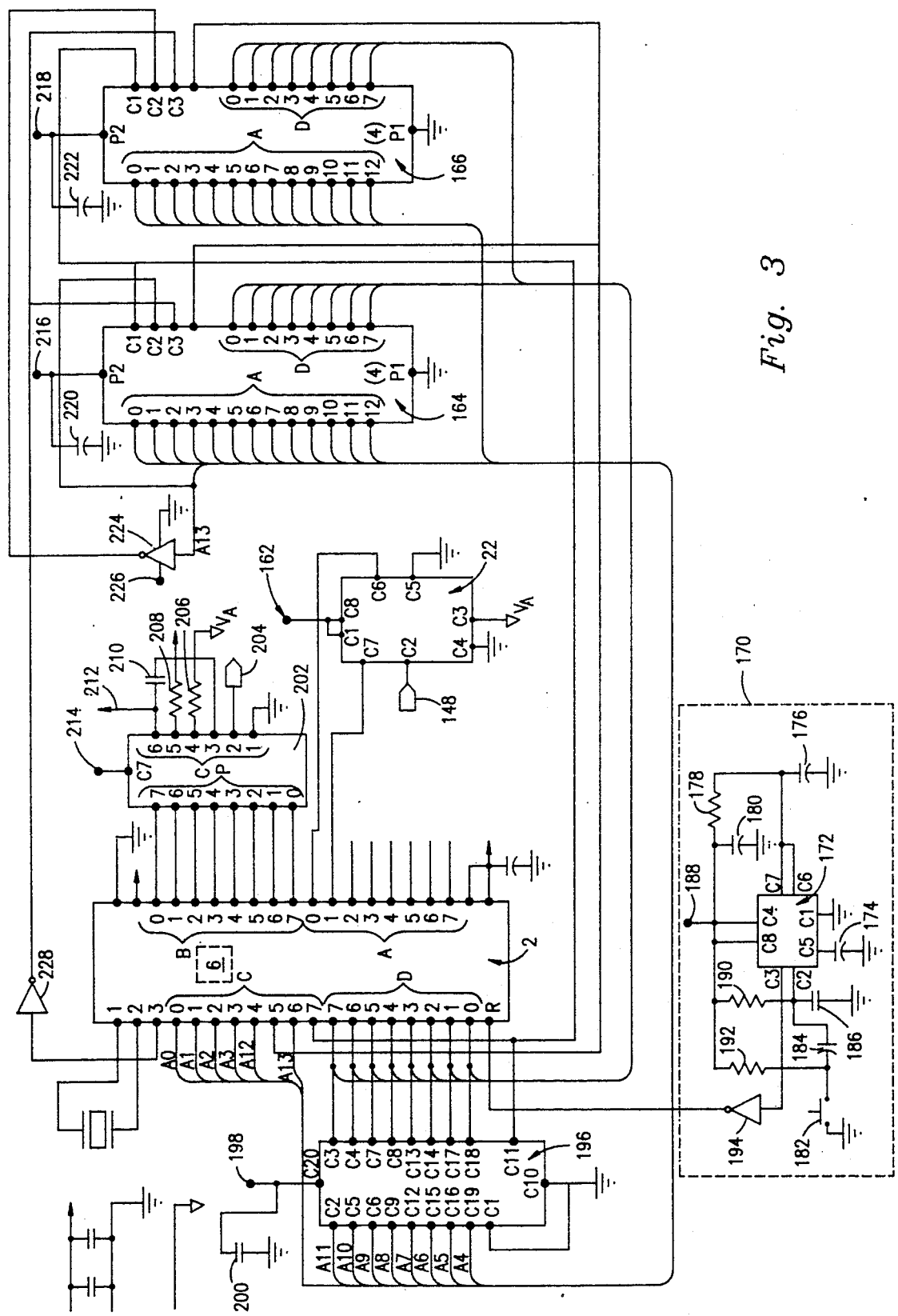
FIG. 3 is a schematic diagram of one embodiment of digital circuitry which may be used in the cardiac event monitoring unit and arrhythmia analysis module worn by the patient.

The digital portion of the circuitry of the invention is shown for one embodiment in substantial detail in FIG. 3. Another, preferred, embodiment of the digital circuitry portion of the invention is illustrated schematically in FIG. 10.

In the embodiment of the digital circuitry portion of the invention shown in FIG. 3, analog-to-digital converter 22 is preferably a serial eight bit TLC5491P unit available from Texas Instruments. In the preferred embodiment of the digital circuitry of the invention shown in FIG. 10, analog-to-digital converter 22' is preferably a serial 10 bit TLC 1541 unit available from Texas Instruments.

The conditioned analog electrocardiogram signal, provided via the analog circuitry illustrated generally in FIG. 4, is provided as input to the digital circuitry of the invention, one embodiment of which is illustrated in FIG. 3, by switch 148 connecting to analog-to-digital converter 22 as illustrated. Analog-to-digital converter 22 preferably has eight connections indicated C1 through C8 in FIG. 3. The conditioned analog input is provided via switch 148 to connection C2. Connections C1 and C8 of analog-to-digital converter 22 are connected to a positive constant voltage, preferably five volt, reference which is the source of power for the digital circuitry portion of the invention. Connections C4 and C5 of analog-to-digital converter 22 are preferably connected to the digital ground or reference for the digital circuitry portion of the invention. Connection C3 of analog-to-digital converter 22 is preferably connected to the analog ground reference voltage. Output of analog-to-digital converter 22 is provided via terminal C6. Terminal C7 of analogto-digital converter 22 connects to the clock function of microprocessor 2. Node 162 connected to pins C1 and C8 of analog-to-digital converter 22 represents the constant voltage source of power for the digital portion of the circuitry of the invention.

In the embodiment illustrated in FIG. 3, microprocessor 2 may be a Rockwell R65/11EB single chip microcomputer. The Rockwell R65/11EB has four eight bit digital ports, dual real time clocks and serial input and output ports. In FIG. 3, the pins of the four eight bit digital ports are respectively denoted A0 through A7, B0 through B7, C0 through C7 and D0 through D7 respectively, with pins 0 through 7 being bracketed by brackets A, B, C and D respectively. The Rockwell R65/11EB single chip microcomputer which may be used as microprocessor 2 also accepts expandable programmable read-only memory chips. One such chip, a 2732A 4K UVEPROM may be included as program memory 6 illustrated in FIG. 3. Data memory unit 4 may be embodied as two HM6264 chips, designated 164, 166 in FIG. 3; each of these chips provides 8K bites of random access memory thereby defining a 16K bite random access memory as data memory 4. The fact that chips 164 and 166 illustrated in FIG. 3, may together define data memory 4, illustrated in FIGS. 1 and 2, is indicated by the parenthetical enclosure of the integer "4" in each of chips 164, 166 in FIG. 3. While the Rockwell RC65/11EB single chip microcomputer is not CMOS, all of the other digital circuit elements illustrated in FIG. 3 are CMOS, to provide low power usage as noted above.

A digital-to-analog converter chip, may be provided so that the digitized, compressed version of the electrocardiogram signal can be viewed on an oscilloscope or a strip chart recorder for comparison to the analog version of the signal.

Reset circuitry is designated generally 170 in FIG. 3 and includes as its central element a 555 timer. Pin C1 of chip 172 is connected to digital ground as is pin C5 through capacitor 174. Pins C6 and C7 of chip 172 are connected to digital ground through capacitor 176 and to pins C4 and C8 via resistor 178. Pin C8 further connected to digital ground via capacitor 180. Switch 182, when actuated, provides digital ground potential to one side of capacitor 184, the other side of which is connected to pin C2. Node 188 represents a source of constant voltage potential, preferably positive five volts for the power voltage source for the components of the digital circuitry of the invention. This potential is dropped via resistors 190, 192 for application to a line providing reset input control to pin C2, as illustrated. Output of reset circuitry 170 is provided at pin C3 and is amplified using operational amplifier 194 for input to a reset terminal of microprocessor 2, designated R.

With reference to FIG. 3, control of the address portions of random access memory accessed by microprocessor 2 is provided by chip 196, having twenty connector pins, denoted C1 through C20 respectively. Pins C1 and C10 of chip 196 are connected to digital ground. Pin C20 is connected to an external node 198 which is preferably the constant voltage power source for the digital circuitry of the invention, preferably a reference voltage of +5 volts DC. Pin 20 is further connected to ground via a capacitor 200. Pin C11 of chip 196 is connected to pin C7 of microprocessor 2 which controls external memory selection. These two pins are, in turn, connected to appropriate control pins of random access memory chips 164 and 166; these control pins are designated C1 in chips 164, 166 in FIG. 3. Pin connections C2, C5, C6, C9, C12, C15, C16 and C19, shown extending vertically downward from the top of chip 196 on the left-hand side thereof in FIG. 3, together with pin connections C0 through C4 and C6 from microprocessor 2, define an address bus for thirteen address pins of chips 164, 166 respectively. The address pins of chips 164, 166 are identified as $A_0$ through $A_{12}$ on each of those chips; the respective address pins (to which the respective pins of microprocessor 2 and address control chip 196 are connected) are indicated by corresponding address pin letters appearing (on the connecting lines to the left of microprocessor 2 and to the left of address control chip 196 in FIG. 3) as addresses A0 through A12 respectively. Additionally, information from pin C6 of microprocessor 2 is provided at address A13 to respective control pins of random access memory chips 164, 166, to control which of chips 164, 166 is addressed during a given transfer of data. Control pins of chips 164, 166 (to which the information from pin C6 of microprocessor 2 is provided) identified generally as A13 are designated C2 in each of random access memory chips 164, 166.

Still referring to FIG. 3, output from microprocessor 2 is provided to digital-to-analog converter chip 202 via digital output ports B0 through B7 of microprocessor 2. In addition to eight pin connectors (designated P0 through P7 in FIG. 3) receiving output signal from microprocessor 30, chip 202 has seven additional pin connections designated generally C1 through C7 in FIG. 3. Pin connection C1 is connected to ground. Pin connection P2 C2 the analog output signal indicative of the electrocardiogram being monitored. This cardiogram signal is provided to a connector generally designated 204 in FIG. 3 and similarly designated 204 in FIG. 4. Pin connection C4 is connected to the analog ground reference voltage $V_A$ via a resistor 206 while pin connection P5 is similarly connected to the positive constant voltage .power source for the analog circuitry of the invention, which is preferably plus five volts, via resistor 208. Pin connectors C3 and C6 are connected together via capacitor 210; a lead 212 between pin connector C6 and capacitor 210 leads to the negative of the digital circuitry constant voltage source, which is preferably at −5 volts. Pin connector C7 leads to a node 214 which is preferably maintained at constant voltage of +5 volts by the constant voltage power source for the digital circuitry.

Still referring to FIG. 3 and referring again to random access memory chips 164, 166, data input/output pins are designated D0 through D7 on chips 164, 166; pins D0 through D7 are connected to corresponding data input/output pin connectors D0 through D7 of microprocessor 2. Random access memory chips 164, 166 similarly have pins P1, P2 via which input power is supplied to these chips. Pin connections P1 are connected to ground while pin connections P2 are preferably connected to the digital circuitry power source of constant voltage source at nodes 216, 218. Capacitors 220, 222 connected between digital ground and the lead lines which in turn connect nodes 216, 218 to pins P2 of random access memory chips 164, 166, guard these random access memory chips against surges and spikes. Operational amplifier 224 receives input signal from pin A13 of microprocessor 2 and amplifies that signal for input to control pin C2 of random access memory chip 166. The analog circuitry constant voltage power source, preferably five volts, is connected to operational amplifier 224 as indicated by node 226, provides power to operational amplifier 224.

Control of respective random access memory chips 164, 166 by microprocessor 2 is provided by output pin 3, providing a signal through operational amplifier 228 input to control pins C3 of random access memory chips 164, 166.

Circuitry denoted generally by dotted line box 244 in FIG. 4 receives the cardiogram signal, which has been converted from digital back to analog format and is provided via connector 204. Circuitry 244 includes operational amplifier 246, feedback resistor 248 and provides the amplified analog form signal output to connector 250 for input into an oscilloscope.

In the preferred embodiment of the digital circuitry portion of the invention as shown in FIG. 10, microprocesssor 2' is preferably a Rockwell R65C02 microprocessor. The Rockwell 65C02 has a 16 bit address port, an eight bit data port, a two-phase clock output pin, an interrupt request input line, a reset pin and a read-write control pin. Preferred microprocessor Rockwell R65C02 is illustrated schematically as microprocessor 2' in FIG. 10.

Preferred program memory unit 6' in FIG. 10 is separate from the Rockwell 65C02. The preferred program memory unit is an 8K UVPROM, available from General Instrument, package LCC-32, part number 27C64-20--KA. A preferred data memory unit 4, in the preferred embodiment of the digital circuitry of the invention is preferably embodied as a single HY61-16ALP chip available by Hyundai; this chip provides 2K bytes of random access memory.

The Rockwell R65C02 single chip microcomputer is CMOS, as are all of the other digital circuit elements schematically illustrated in FIG. 10 and collectively defining the preferred embodiment of the digital circuitry of the invention.

Control of the address portions of the random access memory accessed by microprocessor 2' is provided by a decoder chip 5' in FIG. 10 which is preferably a 74 HC138 chip available from National Semiconductor, package SOIC-16, part number MM74HC138M.

A system clock oscillator is defined by a crystal oscillator 11' and a counter 13' illustrated schematically in FIG. 10 as being connected to microprocessor 2' and decoder 5'. Crystal oscillator 11' is preferably a Statek LX0-1.000MHz-C. Counter 13' is preferably a Signetics decade counter sold as a SOIC-16, part number HEF4017BTD. The combined functions of the digital parallel port 12' and the clock-calendar unit 14' are performed, as illustrated in FIG. 10, by a single VIA integrated circuit available from GTE as package PLCC-44, part number G65SC22PE-1.

In the preferred embodiment of the digital circuitry of the invention, a timer 23' is connected to the combined function digital parallel port and clock/calendar unit as illustrated and is preferably a dual timer available unit from Texas Instruments, package SOIC-14, part number TL556CD. To provide the constant voltage source of power for the digital circuitry of the invention, a digital voltage regulator is used. The preferred regulator is available from Maxim, package SO-8, part number MAX663CSA. The preferred embodiment of the digital circuitry of the invention further includes an analog-to-digital converter with multiplexer 22'. The preferred converter is available from Texas Instruments, package PLCC-20, part number TLC1541IFN.

In FIG. 10, the preferred embodiment of the digital circuitry of the invention, similarly to the circuitry illustrated in detail in FIG. 3, microprocessor 2' has an address bus and a data bus where the address bus consists of sixteen lines and the data bus consists of eight lines. The address bus line is indicated by line 400' in FIG. 10 while the data bus line is indicated by 402' in FIG. 10. Data memory unit 4' is connected to lines 400', 402' as shown, as is program memory unit 6' and a combined digital parallel port 12' and clock/calendar unit 14'.

The apparatus of the invention preferably includes three different voltage regulators, one to run the analog circuitry, one voltage regulator to supply power to the analog circuitry components, a second voltage regulator to supply operating power to the digital circuitry components and the third voltage regulator to run the motor of the tape drive. All three voltage regulators are powered by the batteries.

Referring again to FIG. 3, decoder unit 196 selects either of chips 164, 166 by the chip select port for addressing by microprocessor 2. In FIG. 3, amplifier 224 functions as an invertor to control which of chips 164, 166 is active. Amplifier 228 in FIG. 3 acts as an invertor and supplies a clock function to chips 164, 166. Further referring to FIG. 3 and additionally to FIG. 4, the small schematics in the upper lefthand corner of these figures respectively represent the voltage regulators supplying power to the circuit components shown in those drawings. Neither of those voltage regulators nor the individual components thereof are numbered in the drawings.

Referring again to FIG. 10, the crystal oscillator 11' and counter 13' define an oscillator circuit with crystal oscillator 11' providing 1 MHz square pulses having a fifty percent duty cycle. Counter 13' passes every tenth pulse, resulting in a 100 KHz clock signal having a five percent duty cycle. The clock pulse widths are preferably 0.5 microseconds. This is a significant advantage because the CMOS integrated circuits illustrated in FIG. 10 consume most of their power while the clock pulse is high. By reducing the duty cycle of the clock signal, significant proportional savings in power are achieved.

Another way in which power is conserved is that the digital circuitry of the invention in the preferred embodiment illustrated in FIG. 10 runs microprocessor 2' at the slowest clock frequency possible, which is 100 KHz, to accomplish the microprocessor's task because circuits such as microprocessor 2' consume power proportionally to the applied clock frequency. Microprocessor 2' embodied as the Rockwell R65C02 microprocessor uses a VIA (Versatile Interface Adapter) defining digital parallel port 12' and clock/calendar unit 14, to interface with the other integrated circuits.

To further conserve power, the clock signal is turned off at times, to put the integrated circuits illustrated in FIG. 10 in a very low power standby mode. This turn-off of the clock signal is performed by microprocessor 2' under program control according to predetermined criteria. One such criteria may be when no signal input from the electrocardiogram electrodes is present. The infrared sensing transistor and diode unit has the capability to restart the clock circuit, waking up the entire cardiac monitor unit.

In the analog circuitry, bandwidth is from 0.1 to 50 Hz in the preferred embodiment of the analog circuit portion of the invention as illustrated in FIGS. 5 through 9.

Control of the tape recorder motor is achieved through use of a regulator supplied by Maxim, package SO-8, part number MAX663CSA.

In both embodiments of the invention, the tape recorder has magnetic read and write heads which are preferably the same, with each head capable of both read and write functions. One set of heads may be used, having a 65 microinch gap between them, permitting a high pulse packing factor. Each cardiac monitoring unit preferably contains one magnetic recorder head. Each cardiac monitor unit also preferably has at least one playback unit, including the second magnetic recording/writing head.

The design goal is to have mechanical operation of the playback unit to be similar but not identical to that of the recorder unit. Preferably, the playback unit first rewinds a tape taken from the cardiac monitor unit. The playback unit then plays the tape, via an interface unit, into the computer and ancillary thereto, onto the base station computer's hard disk at high speed. The design goal for playback tape speed is to be approximately five inches/second, giving a peak playback frequency of about 22.5 KHz. Thus, a full tape, which can represent 188 days of records when recording cardiac monitor data according to this invention, should be played back in about 56 minutes. This is a record/playback ratio of 29,571:1.

The cardiac monitor unit preferably accepts standard, commercially available microcassettes capable of 60 or 90 minutes of recording at a tape speed one 1.2 centimeters per second. The tape recorder drive system is essentially silent when operating, to avoid annoying distractions causing concern to the patient wearing the cardiac monitor unit and the arrhythmia analysis module. Because there are sometimes long periods between individual tape movements, the tape drive system preferably does not contain any component which takes a "set" in a particular position. The problem of "set" is a subtle but important problem in tape drive systems in which capstans and pressure rollers are used. "Set" is especially a problem in systems in which the tape is maintained in a single position for a long time followed by a very small linear movement of the tape. By designing the apparatus of the invention without components tending to take a "set" in a particular position, this problem is avoided. Drive system torque requirements for the tape recorder motor are low, to avoid using available electrical power.

The tape guidance system prevents all but a negligible amount of transfer tape motion, to maintain recorded bit registration across the tape during recording and playback. This is important since the playback unit is not the same mechanical unit as performs the recording. Hence, bit registration is exceedingly important. Unless careful consideration is given to maintaining bit registration, lack of bit registration can be a problem, particularly when very thin magnetic tapes, having greater data capacity, are used.

The cardiac monitoring unit preferably incorporates a fourtrack magnetic tape record head for 0.15 inch wide magnetic tape, preferably having a gap width of less than $65 \times 10^{-6}$ inches. Furthermore, it is preferable that the magnetic tape head be able to perform both recording and playback functions to permit procurement economies. Additionally, the magnetic record and playback head preferably has impedance characteristics such that optimal magnetic polarity-reversal pulses require minimum power.

The tape drive system has been designed with a design goal of recording with a packing factor greater than or equal to 4,500 bits/inch/track, for a bit spacing of less than $222.2 \times 10^{-6}$ inches, which is $65.44 \times 10^{-4}$ millimeters. This packing factor requires that the system have virtually no backlash between the drive system actuator and the capstan and further that there be no slippage between the drive system actuator and the capstan should a stepping-type actuator be used.

The cassette reel accepting the recorded tape is preferably driven so that tape take-up occurs with "overdrive." This reel is preferably driven with an interposed slip clutch between the reel and the motor.

The playback unit mechanical design is preferably capable of playback tape speeds on the order of 5 inches per second or 12.7 centimeters per second.

The preferred embodiment of the tape system uses a standard precision worm and worm gear, notwithstanding their weight and size. A relay-motor-driven ratchet gear (having six degree increments) combination is used. All shafting is precision ground stainless steel ground to a diameter of 0.1248 inches plus 0.000 inches minus 0.0002 inches. All bearings used are precision, miniature ball-bearings. Standard high pitch precisions cut gears, made of aluminum, are used in the reel take-up mechanism and the slip clutch.

Figure 11:
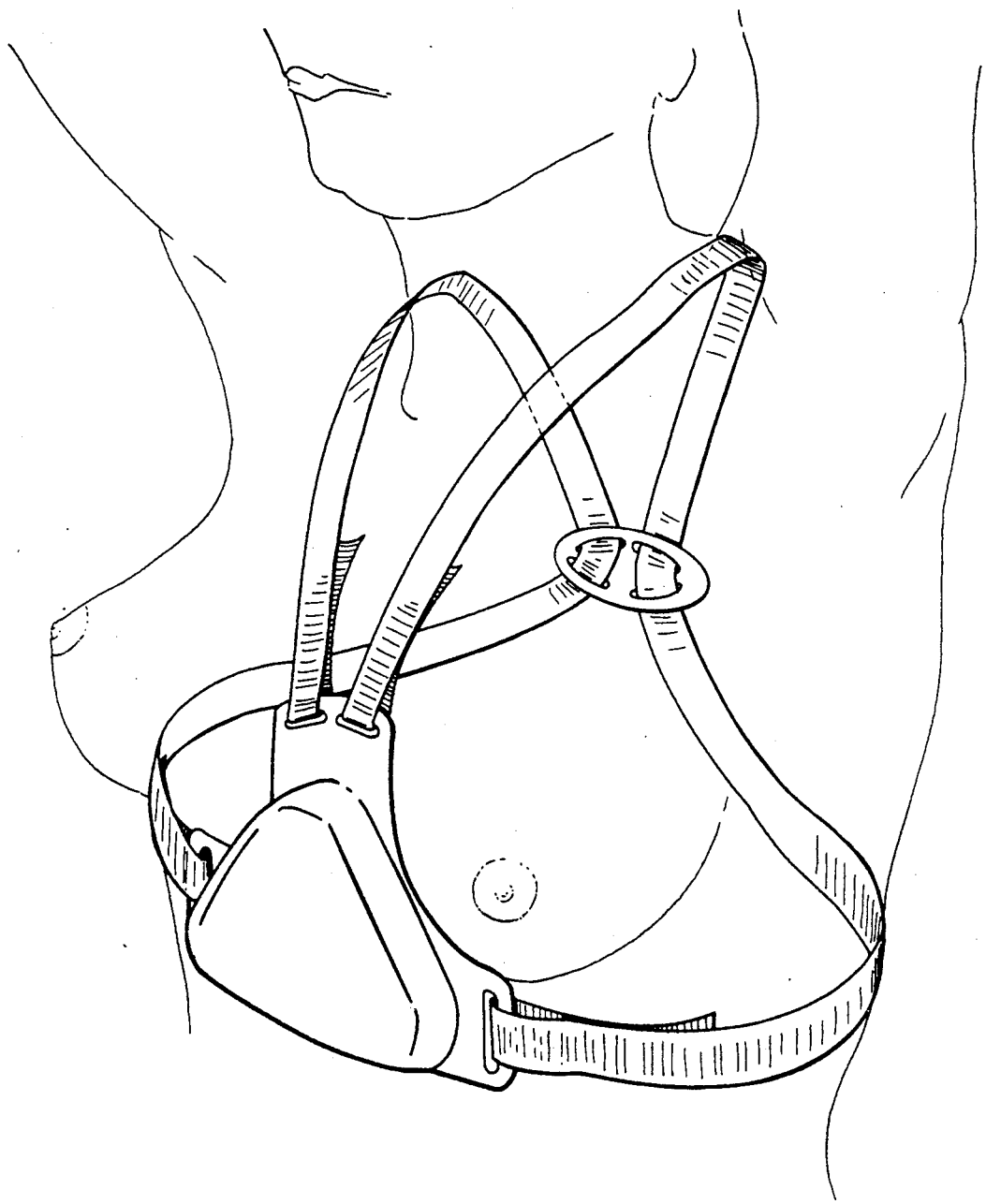
FIG. 11 is a perspective view of the cardiac event monitoring unit/arrhythmia analysis module as worn by the patient.

The outer casing for the cardiac monitor, illustrated in FIG. 11, can be opened by a physician's or clinician's technician to remove the tape cassette. When closed and in use by the patient, the casing is not easily opened by the patient. The alarm chime of the cardiac monitor unit is audible through the outer casing. The casing fits into a fixture supplied with the base station; in this arrangement, a part of the casing, which is facing to the fixture, contains the transmission port for the infrared communications link between the cardiac monitor unit and the base computer. The transmission port has an infrared filter sealed to the casing. The casing around the cardiac monitor infrared port is permanently sealed and waterproof. The electrode feed cable is hermetically sealed at the opening through which the lead passes in the cardiac monitor casing.

The cardiac monitor preferably operates using a pulsed/continuous operation format. This format is extremely efficient in power usage and in timeliness in which data can be written onto the tape. Additionally, such operation eliminates the requirement for large reduction gears and sometimes tricky to manufacture microminiature stepping mechanisms. The cardiac monitor unit is expected to be able to process more than several thousand tapes before the drive motor might have to be replaced; computations have shown this figure to be conservative. Additionally, elimination of an external reduction gear reduces volume of components internal to the cardiac monitor and should make the cardiac monitor manufacturing process considerably simpler than otherwise.

The software components of the invention consist of three types: control software, cardiac event recognition software and data compression software. Data compression software facilitates use of the cardiac monitor unit of the invention as a long term monitor capable of accurately storing a great number of arrhythmic events, as a result of the efficient data storage provided by the data compression software.

The control software provides control of the analog-to-digital converter, management of the random access memory and control of the digital-to-analog converter.

Event recognition in the cardiac monitor is keyed on the detection of the R-wave of the patient's electrocardiogram. While any of a variety of criteria may be used to detect occurrence of the R-wave and thereby trigger the various analysis functions of the invention, one preferred way of detecting the Rwave is to use a combination of the absolute value of the electrocardiogram signal and the absolute value of the slope of the electrocardiogram signal and to analyze this combination according to preselected criteria. This approach has worked well to date.

Data compression techniques are used to convert data into a compact form without destroying any cardiac information. Design of the data compression technique minimizes memory storage through high speed decoding and encoding algorithms.

The ADM data compression technique was selected for use in the cardiac monitor since ADM has such a high data compression ratio. The ADM technique does not produce wave forms with the high fidelity of Huffman coding, but ADM is of high enough fidelity to use in the study of arrhythmias according to the invention.

Because the cardiac monitor of this invention is a miniature long-term monitor, it has been important to establish a projected estimate of power consumption so that battery size and capacity could be estimated in designing the apparatus and utilizing the method of the instant invention. A major independent variable playing a significant role in computing the estimate of battery size and capacity was the number of events to be recorded daily. In the course of projecting the estimated power consumption as a part of battery size and design, it was determined that on a typical day a patient typically using the cardiac monitor of the invention might experience twenty "events", as a conservative number. This data was developed based on analysis of over 1,000 Holter monitors operating over three years. Studies of these events revealed that 99% of those events were under ten seconds in duration; these numbers include numbers for patients who were known to have high frequencies of events.

In the preferred embodiment, the apparatus of the invention records data on the four-track tape portion of the tape recorder. The four-track tape has been prerecorded with "zeros" in every location by a permanent magnet installed in the tape path just before the tape reaches the recording head. When recording, the apparatus of the invention records only "ones." During playback, the base station of the invention depends on the data to selfclock the recording so that speed control is not necessary. For example, the base station computer looks for a "one" in any of the four tracks of the tape. When a "one" is detected, the data is read. The recording technique records the "one" on the tape for duration long enough so that the small amount of the tape skewing expected during playback does not effect the computer reading. Once the computer detects a "one" and the nibble is read, the base station computer does not read another nibble until all four channels have returned to "zero", indicating the end of the current nibble. The computer then awaits the next one as "one" signalling start of the next nibble.

With this approach, at least one of the four channels must contain a "one" to signal presence of a nibble. With data such as date and time, this is no problem because the computer and the base station use codes that do not permit all zeros in an individual nibble. The ADM-processed data presents a problem because it consists of strings of single bits. A study of ADMcoded electrocardiograms shows that about 2% of the time four zeros in a row occur in a nibble.

One way to correct for this situation could be to reserve a track of the tape as a clock signal. For example, one approach might be for every time data is to be written to the tape, to use three channels of the tape for data and one channel for the clock. This scheme, while acceptable, requires one of the four tracks of the tape be dedicated to the clock thereby reducing data recording space by 25%. The approach used in the preferred embodiment of the apparatus manifesting the invention is somewhat different. In the preferred apparatus embodying the invention, the microprocessor is programmed according to a rule stating that if the first three tracks on the tape are "0", a "1" will be recorded in the fourth track. Otherwise, data will be recorded in all four tracks of the tape. The base station of the computer is programmed with the same rule so that if the first three tracks are "0", the "1" in the fourth track of the tape is regarded as a clock signal and is ignored as a data point. This method requires only about a 0.5% reduction in recording space, which is obviously a great improvement over the 25% reduction required if one track of the four tracks on the tape is dedicated to the clock.

Four fundamental types of data are stored on the tape. These are: (1) report identification information, (2) program information, (3) hourly information and (4) event information.

The preferred cardiac monitor unit according to the invention computes and stores heart rate minimum, maximum and mean for each hour as well as other data such as the number of premature complexes, run of tachycardia (either supraventricular or ventricular), periods of traycardia and bradycardia. In addition, the cardiac monitor triggers on several rate and coupling interval limits to record major arrhythmic events. The recording of an electrocardiogram consists of six complexes before onset of an event, twelve complexes immediately after the triggering complex and including the complex triggering the event, six complexes every minute the event is in progress, six complexes immediately prior to the end of the event and six complexes immediately after the event has ended. Information recorded for each event includes time, date and reason for recording the event. The data is stored on the microcassette to be downloaded, at the end of the monitoring period, into the base station computer for subsequent review, formatting and storage. Stated another way, the cardiac monitoring unit continuously monitors the single electrocardiogram lead for cardiac rhythm disturbances. Upon detection of such a disturbance, the device digitally records on magnetic tape the electrocardiogram before, during and after the disturbance. Additionally, the monitor counts premature complexes and records the electrocardiogram for a percentage of such complexes. Hourly, or at some other selected time interval, the cardiac monitor records average heart rate, maximum heart rate and minimum heart rate. In a typical situation, up to three months of such data can be recorded without the need to replace batteries or tape, where a typical situation is one in which the patient has twenty recorded arrhythmic events daily.

The tape recorder portion of the cardiac monitor of the invention preferably uses a Portescap motor which draws twentyfour milliamps during operation. The recording method can lay down data onto the tape at a rate of 1,220 nibbles per second. In a one month period, the motor is turned on once to record certain report identification information and program information for one-tenth of one second. If the recorder is turned on five times daily to record the data taken hourly, in one month the recorder is turned on 150 times for a total of 1.5 seconds. If during that month, 600 events occur with the patient requiring the motor to be turned for a total of 984 seconds or 1.64 seconds per event, total motor running time for one month is approximately 190 seconds. The number of nibbles to be recorded in one such month for one such patient computes to 1,215,112 or 40,504 per day. Because a sixty-minute microcassette tape of the type used in the preferred embodiment of the apparatus of the invention contains about 1,700 inches of tape, such a tape, when written with a packing factor of 4,500 bits per inch per track, has the capacity of 7,650,000 nibbles. From this, it follows that it requires 188 days of typical use to fill a cassette in the cardiac monitor of the invention.

The following table reflects variations on these parameters and illustrates the variation in the number of days which may be required to fill the cardiac monitor of the invention, according to the number of events the patient wearing the monitor experiences in twenty-four hours:

| Number of events/ 24 hours | Number of events to fill tape | Number of days to fill tape |
| --- | --- | --- |
| 20 (1 every 72 min) | 2508 | 188 |
| 30 (1 every 48 min) | 2508 | 126 |
| 40 (1 every 36 min) | 2508 | 94 |
| 50 (1 every 29 min) | 2508 | 75.5 |
| 60 (1 every 24 min) | 2508 | 63 |
| 72 (1 every 20 min) | 2508 | 52.5 |
| 144 (1 every 10 min) | 2508 | 26 |

Many variables affect these estimates. For example, the duration of individual events varies and affects both the number of episodes to fill the tape and the surveillance duration in days. From the cardiologist's point of view, if the number of events increases markedly for each twenty-four hour period, there is likely to be less need for long-term surveillance of the patient.

Because of the long-term approach used by the cardiac monitor of the invention, the electrodes attached to the patient should have the lowest possible impedance so that slight variations in contact impedance produce virtually no motioninduced artifactual signal. Additionally, the material contacting the patient's skin should be biocompatible.

Prior to using the invention, the monitor must be equipped with two AA, preferably lithium batteries, a standard audio microcassette tape and must be programmed. In a typical application such as noted immediately above, this permits the cardiac monitor to operate for at least three months with the 60 minute cassette recording the data over the three-month period.

The cardiac monitor unit of the invention has no switches or user controls. In the preferred operation of the invention, once the batteries are installed, the cardiac monitor unit executes a "cold" start and goes into an initial standby mode in which only one extremely low power circuit is activated. This circuit consists of infrared transistor and diode combination schematically shown and designated 10. This infrared transistor detector is inactive in the absence of infrared light. The infrared transistor detector monitors the signal from the base station computer and wakes up the cardiac monitor apparatus of the invention when the appropriate initialization signal is received from the base station compute via the infrared link.

When the clinician or cardiologist is ready to set the programmable parameters, the cardiac monitor communicates to the base station. The base station preferably consists of a personal computer such as an IBM personal computer, the cardiac rhythm programmer/playback unit and display peripheral devices, such as a graphic screen, printer and/or strip chart recorder/printer.

Prior to communicating with the cardiac monitor, the cardiologist or clinician must select various parameters and enter data for documentation purposes. The set-up program on the personal computer base station guides the user through the operation. Data that might be included in order to operate the method according to the invention might include the following:

1. Patient Name and ID Number
2. Patient Address
3. Patient Phone Number
4. Patient Medication
5. Patient Sex
6. Patient Social Security Number
7. Patient Age
8. Lead Arrangement
9. Current Time (automatically entered by the base station PC)
10. Current Date (automatically entered by the base station PC)
11. Other Notes
12. Tachycardia Limit (e.g. default=150 complexes per minute)
13. Bradycardia Limit (e.g. default=40 complexes per minute)
14. Gradual Rate Change Limit (e.g. default=33% decrease in cycle time)
15. Rapid Rate Change Limit (e.g. default=33% decrease in cycle time)
16. Percentage of Premature Complexes to Record
17. Alarm Options
18. Start/Stop Options All of this data is preferably recorded onto a diskette in the computer and is also recorded in the cardiac monitor. Items 1 through 11 are self-explanatory. Items 12 through 16 define conditions triggering the monitor to record an event on tape, where an event may be defined as six (or some other predetermined number of) complexes prior to the trigger, twelve (or some other predetermined number of) complexes immediately following the recognition trigger, six (or some other predetermined number of) complexes each minute the condition continues, six (or some other predetermined number of) complexes immediately prior to the end of the condition and six (or some other predetermined number of) complexes immediately after the end of the condition. In one preferred operating method of the invention, the six-twelve-six-six-six complex regime has been used successfully.

Data items 12 and 13 as listed above set absolute limits for tachycardia and bradycardia while items 14 and 15 set relative limits for these parameters. Item 14 defines maximum rate at which heart rate can gradually change without triggering the recording of an event. In one preferred practice of the invention, if the difference in average heart rate monitored during the two most recent sets of 15 complexes is greater than the number set as data item 14, an event is triggered. Data item 15 defines maximum rate at which the heart rate can change rapidly without triggering the recording of an event. If the difference of the average heart rate of the two most recent sets of three complexes is greater than the number set as item 15, an event is triggered. Whenever a premature complex occurs, it is counted and the number per hour is recorded on the monitor's tape. While the user, namely the clinician or cardiologist, may not be interested in every premature complex, it may be of interest to record a percentage of such complexes. For example, if the clinician or cardiologist wanted to consider one out of every 100 premature complexes as an event, the clinician or cardiologist would enter "1" for item 16. If all premature complexes were to be recorded on tape, the user would enter "100."

Item 17 sets the alarm options for the cardiac monitor. In the default mode, the audio alarm chimes only when the batteries or tape is low, meaning approximately one day of operation remains, or some other hardware problem is detected, such as an open electrocardiogram lead. At the clinician's or cardiologist's option, the cardiac monitor can also alarm based on detected events. For example, the clinician or cardiologist may want the alarm to sound whenever the absolute heart rate level is triggered. In any event, the cardiac monitor produces different chime patterns for different alarms. The clinician or cardiologist prepares the patient ahead of time for the possibility of an alarm. The patient is told to contact the clinician or cardiologist as soon after an alarm occurs as is possible.

Item 18 permits the time of start and stop operation to be programmed into the cardiac monitor.

Once the data is entered into the base station personal computer, it is recorded on the disk associated with the computer and used to program the cardiac monitor. The cardiac monitor is placed in the programmer unit of the base station personal computer and wireless communication, through the infrared detector, begins with the personal computer. The cardiac monitor case has a small infrared transmission window through which serial communications take place with the computer. These infrared communications eliminate the need for cables and simplify and improve the package design.

When in the communications mode, the base station personal computer continuously sends an infrared "wake-up" signal to the cardiac monitor. The infrared transistor circuit 10 of the cardiac monitor unit recognizes a signal and turns on microprocessor 2 or 2', which goes into the communications state while all other circuits remain "off."

Once the cardiac monitor unit is in the communications state, the base station requests the status of the cardiac monitor. Upon receiving this request, the cardiac monitor unit performs an internal test of all of the circuits and reports the status of those circuits to the base station computer. If a problem exists with any of the cardiac monitor's circuitry, the base station informs the clinician or cardiologist of the problem and provides advice for correction of the problem.

If the cardiac monitor unit performs its self-checkout correctly and no problems appear, the base station transfers the program data to the cardiac monitor. The cardiac monitor then echoes the program data back to the base station to indicate that proper program data receipt has occurred. All of the data is recorded on the cardiac monitor's cassette tape and program variables are stored in program memory unit 6, 6'.

Once the cardiac monitor has been programmed, the cardiac monitor goes into a state awaiting electrocardiogram signals. At this point, the clinician or cardiologist connects the electrocardiogram leads to the patient. The monitor transmits the electrocardiogram through the wireless infrared communication link to the base station personal computer. The electrocardiogram is then displayed "live" on the personal computer screen. This permits the clinician or cardiologist to be assured that the leads are properly attached to the patient and that the cardiac monitor is receiving a good signal. These "live" signals are also recorded on a disk in the personal computer so it can be known that the critical step of assuring an operating "live" electrocardiogram lead connected to the cardiac monitoring unit was, in fact, checked prior to dismissing the patient. When satisfied with the operation, the base station computer sends a sign-off signal to the cardiac monitor at which time the cardiac monitor begins the independent operation.

During operation, the cardiac monitor unit constantly monitors the electrocardiogram of the patient. The electrocardiogram signal is digitized, by the analog-to-digital converter 22, 22' at a rate of 200 times per second. The data is compressed and stored in the random access memory. Data for the most recent six or more (or some other predetermined number of) complexes are always kept in the random access memory 4 or 4'. Additionally, once per hour, the following data are stored on the cassette tape: Date, time, average heart rate for the hour, minimum 15-beat (or some other preselected number) average heart rate for the hour (or some other preselected time interval), maximum 15-beat (or some other preselected number) average heart rate for the hour (or some other preselected time interval) and the number of premature complexes occurring during the hour (or some other preselected time interval). Of course, other recording parameters, recording frequencies, consecutive beat recording criteria and the like may be chosen.

In the preferred mode of operation of the invention, data is recorded on the tape whenever an event is triggered, as defined by preselected criteria. Using one preferred preselected criteria, an event is triggered by (1) the most recent 15-beat average falling below the low heart rate trigger or (2) the most recent 15-beat average exceeding the high heart rate trigger, or (3) detection of a change in heart rate greater than the gradual limit (e.g. the difference between the most recent 15-beat average and the previous 15-beat average exceeding the programmed limit), or (4) detection of a change in rate greater than the rapid limit, e.g. the difference between the most recent three beat average and the previous three beat average exceeding the programmed limit, or (5) a premature complex occurring that is be recorded, i.e. in the case of a criteria whereby one percent of the premature complexes are to be recorded, the system records hundredth premature complex.

In the preferred practice of the invention, for each event, the following is recorded on tape: Time, date, the criterion the monitor used in determining to record the event (for example, high rate trigger exceeded), the most recent 15-beat heart rate average, the electrocardiogram for the six beats prior to the trigger, the electrocardiogram for the twelve beats starting with and immediately after the trigger (so as to include the trigger), six beats of the electrocardiogram every minute the condition that caused the trigger prevails, six beats of the electrocardiogram immediately prior to the end of the event and six beats of the electrocardiogram immediately after the event.

With the preferred programming, if the cardiac monitor determines that after five minutes electrocardiogram signals are not present, the cardiac monitor notes the time and date on the cassette tape and reverts to its low power state. While in the low power state, preferably only those circuits required to monitor a return of the electrocardiogram signal receive power. Once the electrocardiogram signal returns, the cardiac monitor notes the date and time on tape and resumes full power, normal operation. This programmed operation conserves power and tape while the cardiac monitor is removed from the patient for any reason, for example, bathing, or if the or the cable between the sensing electrode and the cardiac monitor unit is damaged. An appropriate alarm sounds in any of these cases.

At the end of the scheduled cardiac monitoring period, the patient returns to the base station. At that time the clinician or cardiologist enables the base station and performs a check of the cardiac monitor. The "live" electrocardiogram is again displayed on the base station screen and the cardiac monitor requests permission to perform its diagnostic routines. In this way, the clinician or cardiologist can quickly determine if the cardiac monitor is still operating properly. The electrodes are then removed from the patient and the cassette tape is removed from the cardiac monitor. The tape is then placed in the playback unit of the base station, rewound and the recorded data is played back into the base station personal computer and stored on a disk of the personal computer.

Various cardiac analysis programs can then be executed on the base station personal computer. Standard analysis includes tabulations and charts containing information such as time versus average recorded heart rate, time versus minimum required heart rate, time versus maximum recorded heart rate, number of premature complexes, occurrence of events, low absolute heart rate, high absolute heart rate, rapid change in heart rate and gradual change in heart rate (where these last four can all be analyzed as events have occurred). Additional analysis might include tabulations and/or charts of the number of premature complexes versus the average recorded heart rate, the number of premature complexes versus the minimum recorded heart rate, the number of premature complexes as a function of the maximum recorded heart rate, the number of premature complexes as a function of the occurrence of events with low absolute heart rate, high absolute heart rate, rapid change in heart rate and gradual change in heart rate during occurrence of such events being noted.

In addition to such more or less standard analyses, the clinician or cardiologist is able to run custom interactive and batch analyses by calling up individual traces or selected groups of traces for display on the personal computer screen or on a strip chart recorder. Also, due to the data storage capability of the computer, data from prior runs are available for comparison for assistance in diagnosing a particular patient's cardiac state.

In addition to analysis of cardiac rhythmic patterns and analysis of cardiac parameters indicative of cardiac health, other applications for the cardiac monitor of the invention include long-term electrocardiographic monitoring for ST Segment Analysis in the diagnosis of coronary artery disease and in assessment of the treatment of ischemic heart disease. Modification of the cardiac monitor's algorithm, to monitor shifts in ST Segment level and to record events based on the shifts, facilitates such usage.

Additionally, the monitor can be used to monitor heart rate and body temperature in the course of chemotherapy. Another application is in the monitoring, for at least 100 days, of heart rate and body temperature of patients undergoing bone marrow transplants. This assists in early detection of infection which can be critical to survival of such patients. New drug studies, additionally, often require heart rate and body temperature monitoring of ambulatory subjects. Chronobiology, the study of long-term trends in biology, often needs long-term measurement of bodily functions. The cardiac monitor apparatus and method of the invention can be used in all of these applications.

I claim the following:

1. Apparatus for detecting, optionally analyzing, and recording cardiac rhythm disturbances, comprising:
   a. patient wearable means for monitoring cardiac rhythm and processing signals indicative of cardiac rhythm disturbances, comprising:
      i. means for continuously monitoring cardiac rhythm and other parameters of cardiac state via an electrocardiogram lead adapted to be connected to a patient;
      ii. means for detecting presence of a disturbance in said monitored cardiac rhythm;
      iii. means, operative responsively to said disturbance detecting means, for recording the patient's electrocardiogram before, during and after the detected disturbance;
   b. a base station means for receiving said recorded electrocardiogram for analyzing said electrocardiogram and said additional data which are indicative of cardiac function.

2. Apparatus of claim 1 wherein said means, operative responsively to said disturbance detecting means, for recording the patient's electrocardiogram before, during and after the detected disturbance, includes means for periodically recording data, additionally to cardiac rhythm, indicative of cardiac function.

3. Apparatus of claim 2 wherein said means, operative to said disturbance detecting means, for recording the patient's electrocardiogram before, during and after the detected disturbance, records said electrocardiogram on tape.

4. Apparatus of claim 2 wherein said recording means is a digital recording means.

5. Apparatus of claim 1 wherein said base station and said monitoring means are operatively coupled by infrared transmitting and receiving means.

6. Apparatus of claim 1 wherein said monitoring means further comprises means for tabulating cardiac rhythmic events of selected lesser significance according to criteria of disturbance seriousness.

7. Apparatus of claim 6 wherein said means for detecting presence of a disturbance in said monitored cardiac rhythm detects presence of such disturbances according to preselected criteria of disturbance seriousness, excluding disturbances of seriousness less than the preselected criterion.

8. Apparatus of claim 1 wherein said base station means further comprises means for displaying said recorded electrocardiogram and said additional data which are indicative of cardiac function.

9. Apparatus of claim 1 wherein said means for detecting presence of a disturbance in said monitored cardiac rhythm detects presence of such disturbances according to preselected criteria of disturbance seriousness, excluding disturbances of seriousness less than the preselected criterion.

10. Patient wearable apparatus for detecting, analyzing and recording cardiac disturbances, comprising:
   a. means for continuously monitoring at least one periodic recurring electrocardiogram parameter indicative of cardiac state via an electrocardiogram lead adapted to be connected to a patient;
   b. means for detecting presence of a cardiac disturbance as indicated by said monitored at least one cardiac parameter meeting preselected criteria;
   c. means operative responsively to said disturbance detecting means, for recording the patient's at least one electrocardiogram parameter before, during and after the detected disturbance by continuously recording data indicative of said parameter, storing a preselected number of sequentially recorded data indicative of said parameter and discarding least current data indicative of said parameter as current data are stored to replace said least current data and retaining and storing all of aid sequentially recorded data for a preselected period once said disturbance has been detected.

11. Apparatus of claim 10 wherein said means for recording the patient's electrocardiogram further comprises:
   a. a motor driven tape recorder; and
   b. means for generating shaped drive pulses for input to said drive motor;
      wherein said drive motor has a time constant of about 7 milliseconds.

12. Apparatus of claim 11 wherein said tape recorder stores data on said tape at a rate of at least 4,500 bits/inch/track.

13. Apparatus of claim 12 wherein said tape recorder records data on said tape at a spacing of less than 0.0005 inches between adjacent nibbles of recorded data.

14. A method for detecting, analyzing and recording cardiac disturbances, comprising:
   a. continuously monitoring at least one periodic recurring electrocardiogram parameter indicative of cardiac state;
   b. detecting presence of a cardiac disturbance as indicated by said at least one monitored cardiac parameter according to preselected criteria;
   c. recording the electrocardiogram parameter before, during and after the detected disturbance by continuously recording sequential data indicative of said at least one parameter, storing a preselected number of sequentially recorded data indicative of said at least one parameter and discarding less current data indicative of said at least one parameter as current data are stored to replace said less current data but retaining and storing all of sequentially recorded data for a preselected period once said disturbance has been detected.

15. The method of claim 14 further comprising recording said electrocardiogram parameters on a magnetic tape in digital form at a density of at least 4,500 bits/inch/track.

16. The method of claim 15 wherein discrete nibbles of digital data are spaced from one another on said tape a distance of less than 0.0005 inches.

17. The method of claim 14 further comprising:
   a. continuously monitoring a plurality of periodic recurring electrocardiogram parameters indicative of cardiac state;
   b. detecting presence of a cardiac disturbance as indicated by any one of said monitored cardiac parameters meeting preselected criteria;
   c. recording the electrocardiogram parameter before, during and after the detected disturbance by continuously recording data indicative of said parameters, storing at least three sequentially recorded data items indicative of each of said parameters and discarding oldest data items indicative of said parameters as current data items are stored to replace said oldest data items but retaining and storing all of said sequentially recorded data items for all of said parameters for a preselected period once said disturbance has been detected until said disturbance ceases and continuing said recording for a preselected interval after cessation of said disturbance.

18. The method of claim 7 wherein time, date and reason for recording a given event are recorded for each event.

19. The method of claim 18 wherein said parameters are heart rate, tachycardia and bradycardia.

* * * * *